(12) United States Patent
Pandol et al.

(10) Patent No.: US 6,953,786 B2
(45) Date of Patent: Oct. 11, 2005

(54) COMPOSITIONS COMPRISING PLANT-DERIVED POLYPHENOLIC COMPOUNDS AND INHIBITORS OF REACTIVE OXYGEN SPECIES AND METHODS OF USING THEREOF

(75) Inventors: Stephen J. Pandol, Los Angeles, CA (US); Anna Gukovskaya, Agoura Hills, CA (US)

(73) Assignees: The Regents of the University of California, Oakland, CA (US); The United States of America as represented by the Department of Veterans' Affairs, Washington, DC (US)

( * ) Notice: Subject to any disclaimer, the term of this patent is extended or adjusted under 35 U.S.C. 154(b) by 0 days.

(21) Appl. No.: 10/260,609

(22) Filed: Oct. 1, 2002

(65) Prior Publication Data

US 2004/0063648 A1 Apr. 1, 2004

(51) Int. Cl.$^7$ .................. A61K 31/33; A61K 31/35; A61K 31/185; A61K 31/05
(52) U.S. Cl. .................. 514/183; 514/456; 514/576; 514/733
(58) Field of Search ................ 514/456, 457, 514/732, 731, 183, 576, 733

(56) References Cited

U.S. PATENT DOCUMENTS 6,410,061 B1 * 6/2002 Morre et al. ............ 424/729
6,428,818 B1 * 8/2002 Morre et al. ............ 424/729

OTHER PUBLICATIONS

Cecil Textbook of Medicine, 21$^{st}$ edition, vol. 1, Goldman et al., eds., published 2000 by Saunders Co., (PA), pp. 1060–1074.*
Weyant et al, Cancer Research, vol. 61, pp. 118–25, Jan. 2001.*
Lee et al, Cell Death & Diff, vol. 7, pp. 925–32, 2000.*
Vaquero et al, Pancreatology, vol. 2, pp. 217–361 (abstract), 2002.*
Yamamoto et al, J. Clin. Invest., vol. 107, pp. 135–142, 2001.*
Beers et al, Molecular Breeding of Woody Plants, pp. 43–52, 2001.*
Ahmad, N., et al. (2000) "Green Tea Polyphenol Epigallocatechin–3–Gallate Differentially Modulates Nuclear Factor κB in Cancer Cells Versus Normal Cells", Archives of Biochemistry and Biophysics, vol. 376, No. 2, pp. 338–346.
Babior, B.M (1999) "NADPH Oxidase: An Update" Blood, vol. 93, No. 5, pp. 1464–1476.
Balla, T. (2001) "Pharmacology of Phosphoinositides, Regulators of Multiple Cellular Functions" Current Pharmaceutical Design, vol. 7, pp. 475–507.

Bos, J. L. (1989) "ras Oncogenes in Human Cancer: A Review", Cancer Research, vol. 49, pp. 4682–4689.
Bravo, L. (1998) "Polyphenols: Chemistry, Dietary Sources, Metabolism, and Nutritional Significance" Nutrition Reviews, vol. 56, No. 11, pp. 317–333.
Cohen, J. (1993) "Overview: Mechanisms of apoptosis", Immunology Today, vol. 14, No. 3, pp. 126–130.
Crompton, M. (1999) "The mitochondrial permeability transition pore and its role in cell death", Biochemical Society, vol. 341, pp. 233–249.
Davis, Jr., W. et al., (2000) "Cellular Thiols and Reactive Oxygen Species in Drug–Induced Apoptosis", The Journal of Pharmacology and Experimental Therapeutics, vol. 296, No. 1, pp. 1–6.
DiMagno, E. et al., (1999) "AGA Technical Review on the Epidemiology, Diagnosis, and Treatment of Pancreatic Ductal Adenocarcinoma", American Gastroenterological Association, vol. 117, No. 6, pp. 1464–1484.
Sussman, J. et al., (1995) "The death domain: a module shared by proteins with diverse cellular functions", TIBS, pp. 342–344.
Flohé, L., et. al., (1997) "Redox Regulation of NF–Kappa B Activation", Free Radical Biology & Medicine, vol. 22, No. 6, pp. 1115–1126.
Freeman, B. et al., (1982) "Free Radicals and Tissue Injury", Laboratory Investigation, vol. 47, No. 5, pp. 412–426.
Goldman, R. et al, (1997) "Activation of Map Kinases, cPLA$_2$, and Reactive Oxygen Species Formation By EGF and Calcium Mobilizing Agonists in a Human Keratinocyte Cell Line", Eicosanoids and other Bioactive Lipids in Cancer inflammation and Radiation Injury 3, pp. 289–293.
Green, D. (1998) "Apoptotic Pathways: The Roads to Ruin" Cell, vol. 94, pp. 695–698.
Green, D. et al, (1998) "Mitochondria and Apoptosis" Science, vol. 281, pp. 1309–1312.
Gukovskaya, A. et al., (1996) "Mechanisms of Cell Death After Pancreatic Duct Obstruction in the Opossum and the Rat" American Gastroenterlogical Association, vol. 110, pp. 875–884.
Gukovskaya, A. et al., (1997) "Pancreatic Acinar Cells Produce, Release, and Respond to Tumor necrosis Factor–α" The Journal of Clinical Investigation, vol. 100, 1853–1862.

(Continued)

Primary Examiner—Raymond J. Henley, III
(74) Attorney, Agent, or Firm—Suzannah K. Sundby; Smith, Gambrell & Russell, LLP

(57) ABSTRACT

Disclosed are methods for treating, preventing, or inhibiting cancer in a subject comprising administering at least one polyphenolic compound and at least one inhibitor of reactive oxygen species to the subject. The polyphenolic compound may be derived or isolated from plants. In some embodiments, the polyphenolic compound is a flavonoid. In other embodiments, the polyphenolic compound is a non-flavonoid. Other methods and kits are also disclosed as well as pharmaceutical compositions.

16 Claims, 11 Drawing Sheets

OTHER PUBLICATIONS

Gupta, S. (2000) "Growth Inhibition, Cell–Cycle Dysregulation, and Induction of Apoptosis by Green Tea Constituent (–) Epigallocatechin–3–gallate in Androgen–Sensitive and Androgen–Insensitive Human Prostate Carcinoma Cells" Toxicology and Applied Pharmacology, vol. 164, pp. 82–90.

Hotz, H. et al., (2001) "An Improved Clinical Model of Orthotopic Pancreatic Cancer in Immunocompetent Lewis Rats" Pancreas, vol. 22, No. 2, pp. 113–121.

Hsieh, Tze–chen et al., (1999) "Differential Effects on Growth, Cell Cycle Arrest, and Induction of Apoptosis by Resveratrol in Human Prostate Cancer Cell Lines" Experimental Cell Research, vol. 249, pp. 109–115.

Hsu, H. et al., (1995) "The TNF Receptor I–Associated Protein TRADD Signals Cell Death and NF–κB Activation" Cell, vol. 81, pp. 495–504.

Huang, C. et al., (1999) "Resveratrol Suppresses Cell Transformation and Induces Apoptosis Through a p53–dependent Pathway" Carcinogenesis, vol. 20, No. 2, pp. 237–242.

Hsu, H. et al., (1996) "TRADD–TRAF2 and TRADD–FADD Interactions Define Two Distinct TNF Receptor 1 Signal Transduction Pathways" Cell, vol. 84, pp. 299–308.

Islam, S. et al., (2000) "Involvement of Caspase–3 in Epigallocatechin–3–gallate–Mediated Apoptosis of Human Chondrosarcoma Cells" Biochem. And Biophys Research Comm., vol. 270, pp. 793–797.

Jang, M. et al., (1997) "Cancer Chemopreventive Activity of Resveratrol, a Natural Product Derived from Grapes" Science, vol. 275, pp. 218–220.

Kandel, E. et al., (1999) "The Regulation and Activities of the Multifunctional Serine/Threonine Kinase Akt/PKB" Experimental Cell Research, vol. 253, pp. 210–229.

Kane, L. et al., (1999) "Induction of NF–κB by the Akt/PKB Kinase" Current Biology, vol. 9, No. 11, pp. 601–604.

Katada, T. et al., (1999) "Synergistic Activation of a Family of Phospphoinositide 3–kinase via G–protein Coupled and Tyrosine Kinase–related Receptors" Chemistry and Physics of Lipids, pp. 79–86.

Kong, Q. et al., (1998) "Antioxidant Inhibitors for Cancer Therapy" Medical Hypotheses, vol. 51, pp. 405–409.

Kroemer, G. et al., (2000) "Mitochondrial Control of Cell Death" Natural Medicine, vol. 6, No. 5, pp. 513–519.

LaCasse, E. et al., (1998) "The Inhibitors of Apoptosis (IAPs) and Their Emerging Role in Cancer" AE Mackenzie, pp. 3247–3259.

Leevers, S. (1999) "Signalling Through Phosphoinositide 3–kinases: The Lipids Take Centre Stage" Cell Biology, pp. 219–225.

Lepri, E., et al., (2000) "N–Acetylcysteine Increases Apoptosis Induced by $H_2O_2$ and mo–antiFas Triggering in an 3DO Hybridoma Cell Line" Cell Biochem, vol. 18, pp. 201–208.

Li, H. et al., (2000) "Green Tea Polyphenols induce Apoptosis in Vitro in Peripheral Blood T Lymphocytes of Adult T–Cell Leukemia Patients" Jpn. J.Cancer Res., vol. 91, pp. 34–40.

Lin, K. et al., (1999) "Decreased Intracellular Superoxide Levels Activate Sindbis Virus–induced Apoptosis" Journal of Biological Chemistry, vol. 274, No. 19, pp. 13650–13655.

Madrid, L. et al., (2001) "Akt Stimulates the Transactivation Potential of the RelA/p65 Subunit of NF–κB through Utilization of the IκB Kinase and Activation of the Mitogen–activated Protein Kinase p38" Journal of Biological Chemistry, vol. 276, pp. 18934–18940.

McDade, T. et al., (1999) Salicylates Inhibit NF–κB Activation and Enhance TNF–a–induced Apoptosis in Human Pancreatic Cancer Cells, Journal of Surgical Research, vol. 83, pp. 56–61.

Madrid, L. et al., (2000) "Akt Suppresses Apoptosis by Stimulating the Transactivation Potential of the RelA/p65 Subunit of NF–κB" Molecular and Cellular Bio., pp. 1626–1638.

Mourai, M. et al., (2002) "Food–derived Polyphenols Inhibit Pancreatic Cancer Growth Through Mitochondrial Cytochrome C Release and Apoptosis", Int. J. Cancer, vol. 98, pp. 761–769.

Nakamura, H. et al., (1997) Redox Regulation of Cellular Activation Anu. Rev. Immunol., vol. 15, pp. 351–369.

Norell, S. et al., (1986) "Diet and Pancreatic Cancer: A Case–Control Study" American Journal of Epidemiology, vol., 124, No. 6, pp. 894–902.

Ozes, O. et al., (1999) NF–κB Activation By Tumor Necrosis Factor Requires the Akt Serine–threonine Kinase, Nature, vol. 401, pp. 82–85.

Paschka, A. et al., (1998) "Induction of Apoptosis in Prostate Cancer Cell Lines By The Green Tea Component, (–)–epigallocatechin–3–gallate", Cancer Letters, Vo. 130, pp. 1–7.

Pastorino, J. et al., (1998) "The Overexpression of Bax Produces Cell Death upon Induction of the Mitochondrial permeability Transistion", Journal of Bio. Chem., vol. 273, No. 23, pp. 7770–7775.

Raff, Martin, (1998) "Cell Suicide for Beginners", Nature, vol. 396, pp. 119–122.

Rhee, Sue, (1999) "Redox signaling: Hydrogen Peroxide as Intracellular Messenger", Experimental and Molecular Medicine, vol. 31, No. 2, pp. 53–59.

Romashkova, J. et al., (1999) "NF–κB is a Target of AKT in Anti–apoptotic PDGF Signalling", Nature, vol. 401, pp. 86–90.

Royall, J. et al., (1992) "Evaluation of 2',7'–Dichlorofluorescin and Dihydrorhodamine 123 as Fluorescent Probes for Intracellular $H_2O_2$ in cultured Endothelial Cells", Archives of Biochemistry and Biophysics, vol. 302, No. 2, pp. 348–355.

Sakagami, H. et al., (2000) "Induction of Apoptosis by Flavones, Flavonols (3–Hydroxyflavones) and Isoprenoid–Substituted Flavonoids in Human Oral Tumor Cell Lines", Anticancer Research, vol. 20, pp. 271–278.

Salvesen, G., et al., (1997) "Caspases: Intracellular Signaling by Proteolysis", Cell, vol. 91, pp. 443–446.

Sandoval, D. et al., (1996) "The Role of Neutrophils and Platelet–activating Factor in Mediating Experimental Pancreatitis", Gastoenterology, vol. 111, pp. 1081–1091.

Steinmetz, K. et al., (1991) "Vegetables, fruit, and cancer. I. Epidemiology", Cancer Causes and Control, vol. 2, pp. 325–357.

Subbaramaiah, K., et al., (1998) "Resveratrol Inhibits Cyclooxygenase–2 Transcription and Activity in Phorbol Ester–treated Human Mammary Epithelial Cells", The Journal of Biological Chemistry, vol. 273, No. 34, pp. 21875–21882.

Surh, Y. et al., (1999) "Resveratrol, an Antioxidant Present in Red Wine, Induces Apoptosis in Human Promyelocytic Leukemia (HL–60) Cells", Cancer Letters, vol. 140, pp. 1–10.

Szatrowski, T. et al., "Production of Large Amounts of hydrogen peroxide by human Tumor Cells", Cancer Research, vol. 51, pp. 794–798, date not available.

Thannickal, V. et al., (2000) "Ras–dependent and Independent Regulation of Reactive Oxygen Species by Mitogenic Growth Factors and TGF–β1", The FASEB Journal, vol. 14, pp. 1741–1748.

Thannickal, V. et al., (2000) "Reactive Oxygen Species in Cell Signaling", Am J. Physiol Lung Cell Mol. Physiol, vol. 279, pp. L1005–L1028.

Thompson, Craig, (1995) "Apoptosis in the Pathogenesis and Treatment of Disease", Science, vol. 267, pp. 1456–1462.

Todd, K. et al., "Pancreatic Adenocarcinoma", Chapter 95, pp. 2178–2193, date not available.

Tsai, S. et al., (1999) "Suppression of Nitric Oxide Synthase and the Down–Regulation of the Activation of NFκB in Macrophages by Resveratrol", British Journal of Pharmacology, vol. 126, pp. 673–680.

Wang, C. et al., (1999) "NF–κB Induces Expression of the Bcl–2 Homologue A1/Bfl–1 to Preferentially Suppress Chemotherapy–Induced Apoptosis", Molecular and Cellular Biology, vol. 19, No. 9, pp. 5923–5929.

Wang, C. et al., (1996) "TNF–and Cancer Therapy–Induced Apoptosis: Potentiation by Inhibition of NF–κB", Science, vol. 274, pp. 784–787.

Wang, I. et al., (1999) "Induction of Apoptosis by Apigenin and Related Flavonoids Through Cytochrome c Release and Activation of Caspase–9 and Caspase–3 in Leukaemia HL–60 Cells" European Journal of Cancer, vol. 35, No. 10, pp. 1517–1525.

Wolf, B. et al., "Defective Cytochrome $c$–dependent Caspase Activation in Ovarian Cancer Cell Lines Due to Diminished or Absent apoptotic Protease Activating Factor–1 Activity" The Journal of Biological Chemistry, vol. 276, No. 36, pp. 34244–34251, date not available.

Woo, C. et al., (2000) "Involvement of Cytosolic Phospholipase $A_2$ and the Subsequent Release of Arachidonic Acid, in Signalling by Rac for the Generation of Intracellular Reactive Oxygen Species in Rat–2 Fibroblasts", Biochem. J., vol. 348, pp. 525–530.

Xie, et al., (2000) "Activation of NF–κB by Bradykinin Through a $G\alpha_q$–and Gβγ–dependent Pathway That Involves Phosphoinositide 3–Kinase and Akt", Biological Chemsitry J., vol. 275, No. 32, pp. 24907–24914.

Yin, X. et al., (1999) "Bid–deficient Mice Are Resistant to Fas–induced Hepatocellular Apoptosis", Nature, vol. 400, pp. 886–891.

* cited by examiner

COMPOSITIONS COMPRISING PLANT-DERIVED POLYPHENOLIC COMPOUNDS AND INHIBITORS OF REACTIVE OXYGEN SPECIES AND METHODS OF USING THEREOF

BACKGROUND OF THE INVENTION

1. Field of the Invention

The present invention generally relates to plant-derived polyphenolic compounds, inhibitors of reactive oxygen species (ROS) and compositions thereof and methods for treating, preventing, or inhibiting cancer, such as pancreatic cancer.

2. Description of the Related Art

Pancreatic cancer is the fifth leading cause of cancer death in the United States Cures for this type of cancer are unusual with the cancer recurring as metastatic disease in most cases after the removal of the primary tumor at surgery. See DiMagno EP, et al. (1999) Gastroenterology 117:1464–1484; and Todd K E, et al. (1999) Pancreatic adenocarcinoma. TEXTBOOK OF GASTROENTEROLOGY. Philadelphia: Lippincott Williams & Wilkins, p. 2178–2192.

The development of tumors results from an imbalance between cell proliferation and cell death, apoptosis, and necrosis. See Thompson C B (1995) Science 267:1456–1462. Apoptosis is an active form of cell suicide characterized by a set of events including chromatin condensation, plasma membrane blebbing, cell shrinkage, DNA cleavage by specific endonucleases, and translocation of phosphatidylserine from the inner leaflet of the plasma membrane to the outer leaflet. See Thompson C B (1995); and Cohen J J (1993) Immunol. Today 14:126–130. Phosphatidylserine serves as a marker for macrophages to recognize apoptotic cells and phagocytize them.

There is increasing evidence that one of the major underlying defects in most cancers is an inhibition of normal apoptosis. See Thompson C B (1995) and Cohen J J (1993). Furthermore, treatments such as radiation and chemotherapy act to kill tumor cells and induce tumor shrinkage by causing apoptosis of cancer cells. Apoptosis can additionally be caused by removal of growth factors, the action of specific cytokines, i.e. TNFα, IL-1β, and Fas ligand, and detachment of cells from their extracellular matrix. Recent reports including our own indicate that some polyphenolic phytochemicals are capable of causing apoptosis in cancer cells. See Mouria M, et al. (2002) Int. J. Cancer 98(5):761–769; Hsieh T C and Wu J M (1999) Exp. Cell. Res. 249:109–115; Huang C, et al. (1999) Carcinogenesis 20:237–242; Islam S, et al. (2000) Biochem. Biophys. Res. Commun. 270:793–797; Sakagami H, et al. (2000) Anticancer Res. 20:271–277; Gupta S, et al. (2000) Toxicol. Appl. Pharmacol. 164(1):82–90; Li H C, et al. (2000) Jpn J. Cancer Res. 91(1):34–40; Paschka A G, et al. (1998) Cancer Lett 130:1–7; Wang I K, et al. (1999) Eur. J. Cancer 35:1517–1525; and Surh Y J (1999) Cancer Letters 140:1–10.

Although induction of apoptosis appears to be a promising therapeutic approach to the treatment of cancer, the intracellular mechanisms of apoptosis are incompletely understood. Thus, a need still exists for compositions and methods for inducing apoptosis and treating cancer.

SUMMARY OF THE INVENTION

In some embodiments, the present invention relates to a method of treating, preventing, or inhibiting cancer in a subject comprising administering at least one polyphenolic compound and at least one inhibitor of reactive oxygen species to the subject. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron. In some embodiments, the method further comprises administering at least one antioxidant to the subject. Preferably, the subject is mammalian, more preferably, the subject is human.

In some embodiments, the present invention provides a method of inducing apoptosis in a tumor comprising contacting the tumor with at least one polyphenolic compound. In some embodiments, the method further includes contacting the tumor with at least one inhibitor of reactive oxygen species. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron. In some embodiments, the method further comprises contacting the tumor with at least one antioxidant. In some embodiments, the tumor is a primary tumor. In other embodiments, the tumor is metastatic.

In some embodiments, the present invention provides a method of activating caspase-3 with at least one polyphenolic compound. In some embodiments, the method further includes contacting the protein target with at least one inhibitor of reactive oxygen species. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron. In some embodiments, the method further comprises contacting the protein target with at least one antioxidant.

In some embodiments, the present invention provides a method of activating caspase-3 with at least one polyphenolic compound and at least one inhibitor of reactive oxygen species. In some embodiments, the method further includes contacting caspase-3 with at least one inhibitor of reactive oxygen species. The polyphenolic compound may be derived or isolated from food. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron. In some embodiments, the method further comprises contacting caspase-3 with at least one antioxidant.

In some embodiments, the present invention provides a method of preventing, inhibiting, or modulating NF-κB activation in a cell comprising administering to the cell at least one polyphenolic compound and MG-132, diphenylene iodonium, or both. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the method further comprises administering to the cell at least one antioxidant, at least one proteosomal inhibitor, or both.

In some embodiments, the present invention provides a method of making a cancer cell susceptible to apoptosis induced by a polyphenolic compound comprising inhibiting NF-κB activity in the cell. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol.

In some embodiments, the present invention provides a method of preventing, inhibiting, or attenuating the activation of Akt/PKB in a cell comprising administering to the cell at least one polyphenolic compound, at least one inhibitor of reactive oxygen species and at least one PI 3-kinase inhibitor, or at least one polyphenolic compound and at least one inhibitor of NADPH oxidase or at least one inhibitor of reactive oxygen species. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron. In some embodiments, the method further comprises contacting the cell with at least one antioxidant.

In some embodiments, the present invention provides a pharmaceutical composition comprising at least one polyphenolic compound, at least one inhibitor of reactive oxygen species, and a pharmaceutically acceptable carrier. In some embodiments, the pharmaceutical composition may further comprise at least one antioxidant. In some embodiments, the pharmaceutical composition may further comprise at least one anti-neoplastic agent. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron.

In some embodiments, the present invention provides a kit for treating, preventing, or inhibiting cancer which comprises at least one polyphenolic compound, at least one inhibitor of reactive oxygen species, and instructions for use. In some embodiments, the kit may further comprise at least one antioxidant. In some embodiments, the kit may further comprise at least one anti-neoplastic agent. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron.

In some embodiments, the present invention relates to a method of depolarizing a mitochondrial membrane comprising contacting the mitochondrial membrane with at least one polyphenolic compound and at least one inhibitor of reactive oxygen species. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron. In some embodiments, the method further comprises contacting the mitochondrial membrane with at least one antioxidant.

In some embodiments, the present invention relates to a method of activating mitochondrial permeability transition pore (PTP) comprising contacting the mitochondrial PTP with at least one polyphenolic compound and at least one inhibitor of reactive oxygen species. The polyphenolic compound may be derived or isolated from plants. In some embodiments, the polyphenolic compound is a flavonoid. In other embodiments, the polyphenolic compound is a non-flavonoid. In some preferred embodiments, the polyphenolic compound is selected from the group consisting of flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol. Preferably, the polyphenolic compound is quercetin, rutin, genistein, or trans-resveratrol. In some embodiments, the inhibitor is diphenylene iodonium, N-acetylcysteine, or Tiron. In some embodiments, the method further comprises contacting the mitochondiral PTP with at least one antioxidant.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DETAILED DESCRIPTION OF THE INVENTION

Figure 1:
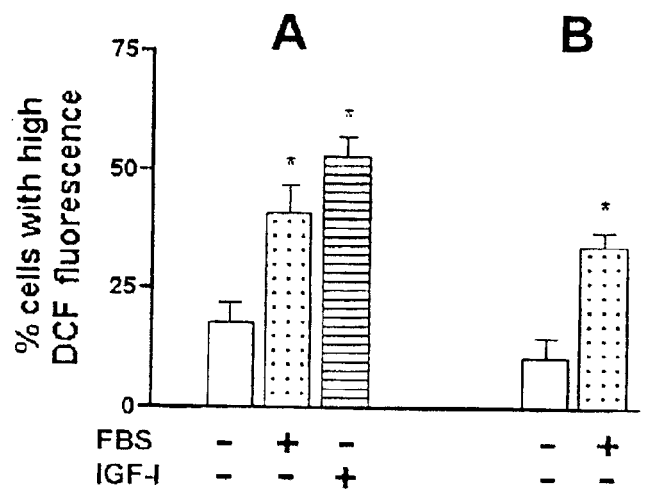
FIG. 1 illustrates that serum and insulin growth factor-1 (IGF-1) stimulate the production of ROS in Mia PACA-2 and PANC-1 pancreatic cancer cells. Mia PACA-2 cells (A); PANC-1 cells (B). Values are means±SE (n=3). $*p<0.05$ compared to cells cultured without serum or IGF-1.

The present invention is directed to compounds, compositions, and methods for treating, preventing, and inhibiting cancer. Specifically, the present invention provides compositions comprising at least one plant-derived polyphenolic compound and at least one inhibitor of reactive oxygen species (ROS) to cause cancer cell death and prevent or treat cancer. The present invention also provides methods for treating or preventing cancer in a subject which comprises administering at least one plant-derived polyphenolic compound and at least one inhibitor of reactive oxygen species (ROS) to the subject.

Additionally, the present invention is directed to inducing apoptosis in cancer cells by modulating phosphatidylinositol 3-kinase Akt/PKB, generators of reactive oxygen species, nuclear factor-κB (NF-κB), mitochondrial permeability transition pore, mitochondrial polarity, mitochondrial cytochrome c release, caspases, or a combination thereof with at least one food-derived polyphenolic compound and at least one inhibitor of reactive oxygen species (ROS).

The invention described in the present application is designed to prevent and treat pancreatic and other cancers. The invention describes the use of combinations of prototype plant-derived polyphenolic compounds and inhibitors of reactive oxygen species to activate death pathways in the cancer cell. This effect on cell death pathways is specific to cancer cells so that normal tissue is unaffected while cancer cells in both primary tumor sites and metastatic sites die. The molecular targets affected by these combinations include phosphatidylinositol 3-kinase Akt/PKB, generators of reactive oxygen species, nuclear factor-κB, mitochondrial permeability transition pore, mitochondrial polarity, mitochondrial cytochrome c release, and caspases. The simultaneous effects of the combination of agents in this invention on these targets leads to cancer cell death. The result is slowing of the growth of the primary tumor as well as prevention of metastases. The invention can be used in strategies for both the prevention and treatment of pancreatic and other cancers.

A. Plant-Derived Polyphenolic Compounds

Evidence from population studies indicates a protective effect of fruits and vegetables in the diet of subjects on cancer. See Steinmetz KA and Potter J D (1991) Cancer Causes Control 2:325–357; and Norell S E, et al. (1986) Am. J. Epidemiol. 124:894–902, which are herein incorporated by reference. Preliminary in vitro and animal experiments suggest that the polyphenolic phytochemical compounds in these foods may be involved in this beneficial effect. See Hsieh T C and Wu J M (1999); Huang C, et al. (1999); Islam S, et al. (2000); Sakagami H, et al. (2000); Gupta S, et al. (2000); Li H C, et al. (2000); Paschka A G, et al. (1998); Wang I K, et al. (1999); Ahmad N, et al. (2000) Arch. Biochem. Biophys. 376:338–346; and Tsai S H, et al. (1999) Br. J. Pharmacol. 126:673–680, which are herein incorporated by reference.

Although there are up to about 8000 plant polyphenolic compounds that have been identified, they can simply be divided into two groups: the flavonoids and the nonflavonoids. See Bravo L (1998) Nutr. Rev. 56:317–333, which is herein incorporated by reference. Flavonoids are characterized as molecules possessing two phenols joined by a pyran (oxygen-containing) carbon ring structure. Common flavonoids include quercetin, rutin and genistein. Flavonoids represent the most common and widely distributed group of plant polyphenolic compounds. Examples of nonflavonoid polyphenolic compounds include the resveratrol family of compounds. Trans-resveratrol has recently received significant attention as a component in red wine and grapes that has anti-tumor and anti-inflammatory properties. See Jang M, et al. (1997) Science 275:218–220; and Subbaramaiah K (1998) J. Biol. Chem. 273:21875–21882, which are herein incorporated by reference. The three polyphenolic compounds used in the Examples herein have the following structural formulas:

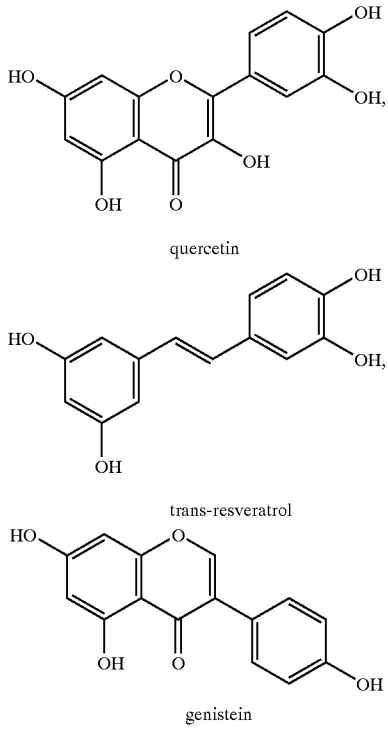

quercetin trans-resveratrol genistein

It should be noted, however, that use of these three polyphenolic compounds is exemplary only and that any polyphenolic compound may be readily used in accordance with the present invention. Polyphenolic compounds of the present invention include compounds that have more than one phenol ring structure. For example, flavenoids, anthrocyanins, anthrocyanidins, isoflavones, catechins, epigallocatechin gallate, gallic acid, chlorgenic acid, curcumin, kaempferol, quercetin, isoquercitrin, myricetin, rutin, pelargonidin, cyanidin, delphinidin, peonidin, malvidin, malvin, oenin, cyanidin, kuromanin, diadzein, daidzin, genitein, genistin, tannic acid, caffeic acid, ferulic acid and traxol, and the like are plant polyphenolic compounds.

As provided in Example 1, quercetin treatment as tested in a nude mouse model of pancreatic cancer using the highly malignant pancreatic cancer cell line, Mia PACA-2, inhibited, prevented, or decreased metastatic cancer lesions. Quercetin treatment also significantly decreased the growth of the primary tumor. Therefore, the present invention provides a method of treating, preventing, or inhibiting cancer, preferably pancreatic cancer, in a subject, preferably human, comprising administering to the subject an effective amount of a polyphenolic compound. The present invention also provides a method of treating, inhibiting, preventing, or decreasing, metastatic cancer lesions in a subject, preferably human, comprising administering to the subject an effective amount of a polyphenolic compound. The present invention further provides a method of treating, inhibiting, or decreasing the growth or growth rate of a primary tumor in a subject, preferably human, comprising administering to the subject an effective amount of a polyphenolic compound. In some preferred embodiments, the polyphenolic compound is quercetin, trans-resveratrol, or genistein.

For the experiments described herein, incubation media free of serum was used in order to determine the effects of the agents in the absence of growth factors. When serum was subsequently added to the incubation conditions, the effects of the polyphenolic compounds described above were attenuated, thereby indicating that agents in serum have an effect on regulating the apoptosis pathways. As provided in Example 2, serum stimulates the formation of reactive oxygen species (ROS) in cancer cells. The presence of serum and insulin growth factor-1 (IGF-1) increases the formation of reactive oxygen species (ROS) in cancer cells, which is inhibited by antioxidants. Therefore, in preferred embodiments, the methods of the present invention further comprise administration of at least one antioxidant.

As provided in Example 3, quercetin, trans-resveratrol and genistein enhance apoptotic cancer cell death in pancreatic cancer cells by causing mitochondrial depolarization and cytochrome c release followed by caspase-3 activation. Inhibition of the mitochondrial PTP resulted in the prevention of mitochondrial depolarization, cytochrome c release, caspase-3 activation and apoptosis. Furthermore, both quercetin and genistein caused inhibition of growth of pancreatic cancer in a nude mouse model. The inhibition was most pronounced on metastatic spread of the tumor and included increased apoptosis in the tumor.

Therefore, the present invention provides a method of inducing apoptosis in a primary tumor comprising contacting the primary tumor with an effective amount of at least one polyphenolic compound. The present invention also provides a method of cleaving a protein target of caspases-3 activation, PARP, comprising contacting PARP with an effective amount of at least one polyphenolic compound.

Also, as described herein, the combination of quercetin and trans-resveratrol caused a synergistic increase in caspase-3 activity. Because quercetin is one of the most potent antioxidants of the polyphenolic compounds, the synergistic effects observed with the combination of quercetin and trans-resveratrol were likely due to the antioxidant effects of quercetin. Therefore, in preferred embodiments, the methods of the present invention further comprise administration of at least one antioxidant.

B. ROS Inhibitors

ROS are produced in large quantities by phagocytes mediating host defense against a variety of microorganisms. See Thannickal, V J and Fanburg, B L (2000) Am J Physiol Lung Cell Mol Physiol 279:L1005-L1028; Freeman, B A and Crapo, J D (1982) Lab Invest 47: 412–426; Rhee, S G (1999) Exp Mol Med 31:53–59; and Babior, B M (1999) Blood 93:1464–1476, which are herein incorporated by reference. There is accumulating evidence that ROS are produced in smaller quantities by non-phagocytes including cancer cells. See Nakamura H, et al. (1997) Annu Rev Immunol 15:351–369 and Davis, W, Jr., et al. (2001) J Pharmacol Exp Ther 296:1–6, which are herein incorporated by reference. At higher concentrations ROS have destructive effects on DNA, proteins and membranes. However, at low concentrations ROS are essential participants in regulation of cell proliferation and survival.

There are multiple potential sources of ROS. The best-characterized source is the NADPH oxidase system in phagocytes. Recent studies suggest that a group of functional proteins analogous to the NADPH oxidase system are present and mediate ROS in non-phagocytic cells. The proteins are called NOX proteins, which are homologous to the NADPH oxidase catalytic subunit, gp91phox. Another source of ROS generation is the mitochondria where ROS are produced as "by-products" of the electron transfer reactions. Other sources of ROS production include oxidation of the phospholipase $A_2$ product, arachidonic acid, by 5-lipoxygenases; and cytosolic xanthine oxidase. See Woo, C H et al. (2000) Biochem J 348 Pt 3:525–530; and Goldman R, et al. (1997) Adv Exp Med Biol 407:289–293, which are herein incorporated by reference.

Although the source of the ROS is not subject of the current invention, it is important to emphasize their potential role and importance in cancer cell survival. First, human cancers produce ROS. See Szatrowski TP and Nathan C F (1991) Cancer Res 51:794–798; Kong Q and Lillehei K O (1998) Med Hypotheses 51:405–409; Thannickal V J, et al. (2000) FASEB J 14:1741–1748; and Bos J L (1989) Cancer Res 49:4682–4689, which are herein incorporated by reference. Second, several cytokines and growth factors have been demonstrated to increase the production of ROS in cancer cells. These include TNFα, TGF-β, IL-1, interferon, PDGF and EGF. Available evidence suggests that the growth factors stimulate ROS by activating NADPH oxidase-like enzyme systems or phospholipase $A_2$ whereas the cytokines stimulate ROS production through mitochondrial mechanisms.

Furthermore, as provided herein, the addition of agents known to decrease the production of ROS caused a decrease in our measurement of cellular ROS using a fluorescent probe technique. For the Examples exemplified herein, three agents that attenuate ROS production were used. The first agent, diphenylene iodonium (DPI), which is a well-established inhibitor of NADPH oxidase, was used because of the likely possibility that the generator of ROS is a NADPH oxidase-like enzyme system. The other two agents were N-acetylcysteine (NAC) and Tiron, which are commonly used to "absorb" ROS.

Also, as provided herein, trans-resveratrol and genistein were found to cause a small increase in ROS production in addition to the effect of serum. Both the effects of serum and the polyphenolic compounds on ROS were prevented by DPI. Thus, serum, trans-resveratrol, and genistein increase ROS in pancreatic cancer cells and that agents known to inhibit ROS production prevent the increases in ROS.

As described herein, the effects of polyphenolic compounds alone and in combination with inhibitors of ROS formation on apoptosis of pancreatic cancer cells was studied. As provided herein, when cancer cells were treated with serum combinations of inhibitors of ROS and polyphenolic compounds resulted in a synergistic increases in cancer cell DNA fragmentation. On the other hand, the combination of DPI with a polyphenolic compound resulted in synergistic increases in DNA fragmentation. The effects of these agents on apoptosis were confirmed by Annexin V staining, which is another measure of apoptosis.

C. Caspases

In the recent past evidence has emerged for key roles for a family of cysteine proteases called caspases, the transcription factor, nuclear factor κB (NF-κB), and phosphatidylinositol 3-kinase (PI 3-kinase) in the mechanism of apoptosis. See Kromer G and Reed J C (2000) Nature Medicine 6:513–519; Salvesen G S and Dixit V M (1997) Cell 91:443–446; and Raff M (1998) Nature 396:119–122; Green D R (1998) Cell 94:695–698; Wang C Y, et al. (1996) Science 274:784–787; Wang C Y, et al. (1999) Mol. Cell. Biol. 19:5923–5929; LaCasse E, et al. (1998); Kane L P, et al. (1999) Curr. Biol. 9:601–604; Romashkova J A, et al. (1999) Nature 401:86–90; Ozes O N, et al. (1999) Nature 401:82–85; Madrid L V, et al. (2000) Mol. Cell. Biol. 20:1626–1638; Xie P, et al. (2000) J. Biol. Chem. 275:24907–24914; and Madrid L V, et al. (2001) J. Biol. Chem. 276:18934–18940, which are herein incorporated by reference.

Caspases are necessary for apoptosis to occur. More than a dozen caspases have been identified. The caspases are synthesized as inactive proenzymes requiring cleavage at Asp residues to be activated. At least some of these caspases can activate each other in the form of a proteolytic cascade. Caspases are generally divided into "initiator" caspases and "executioner" caspases. Caspases-8 and -9 are "initiator" caspases while caspases-3, -6 and -7 are "executioner" caspases.

Recent evidence indicates that there are two distinct pathways that mediate caspase activation and apoptosis. See Hsu H, et al. (1995) Cell 81:495–504; Hsu H, et al. (1996) Cell 84:299–308; Feinstein E, et al. (1995) Trends Biochem. Sci. 20:342–344; Green D R and Reed J C (1998) Science 281:1309–1312; and Yin X M, et al. (1999) Nature 400:886–891, which are herein incorporated by reference. The first one involves the ligation of death receptors, i.e. TNFα R1, Fas, by their ligands resulting in the recruitment of adapter proteins, e.g. Fas activated death domain protein, FADD. See Feinstein E, et al. (1995) Trends Biochem Sci 20:342–344, which is herein incorporated by reference. The receptor-adapter protein complex, in turn, activates caspase-8. This caspase activates downstream "executioner" caspases such as caspase-3.

In the second pathway, various forms of cellular stress cause mitochondrial release of cytochrome c, which binds an adapter protein called APAF1 along with ATP. See Green D R and Reed J C (1998) Science 281:1309–1312; Yin X M, et al. (1999) Nature 400:886–891; and Crompton M (1999) Biochem J 341:233–249, which are herein incorporated by reference. The resulting complex, in turn, binds and activates the "initiator" caspase-9. Caspase-9 then activates downstream "executioner" caspases, i.e. caspase-3. Although these two pathways are initially independent, they share activation of the downstream effector caspases.

Furthermore, there is cross talk between the pathways. For example, caspase-8 cleaves a member of the Bcl-2 family, Bid. This protein then enhances mitochondrial cytochrome c release.

The mechanism of mitochondrial permeabilization and release of cytochrome c is incompletely understood. The permeabilization is usually associated with a loss of mitochondrial transmembrane potential and "opening" of the mitochondrial permeability transition pore (PTP). The PTP inhibitor, cyclosporine A, is frequently used to demonstrate the role of PTP in the involved in apoptosis, i.e. cytochrome c release and caspase activation.

As provided in Example 4, both quercetin and trans-resveratrol convert caspase-3 from its inactive form (32 kDa doublet) to its active form (17 kDa). Additionally, as described herein, caspase-3 activity is synergistically activated with a combination of an inhibitor of ROS production and a polyphenolic compound. Therefore, the present invention provides a method of activating caspase-3 comprising contacting the inactive caspase-3 with at least one ROS inhibitor or at least one polyphenolic compound. In preferred embodiments, the inactive caspase-3 is activated with at least one ROS inhibitor and at least one polyphenolic compound.

As provided in Example 5, quercetin, trans-resveratrol and genistein caused increases in cytosolic cytochrome c and decreases in mitochondrial cytochrome c. In particular, genistein stimulates both apoptosis and caspase-3 activation. Additionally, quercetin, trans-resveratrol, and genistein caused dissipation of mitochondrial membrane potential. Therefore, the present invention provides a method of increasing cytosolic cytochrome c, decreasing mitochondrial cytochrome c, dissipating mitochondrial membrane potential, or a combination thereof, comprising administering to a cell or a subject an effective amount of at least one polyphenolic compound.

D. NF-κB

The mechanisms that mediate the potentiated effects of the polyphenols and inhibitors of ROS on apoptosis were also evaluated. Activated NF-κB may play a role in protecting cells from apoptosis. Many of the effects of NF-κB are thought to be mediated through a group of proteins called inhibitors of apoptosis (IAPs). See LaCasse E, et al. (1998) Oncogene 17:3247–3529, which is herein incorporated by reference. The effects of these mediators are mostly through the regulation of caspases. However, there are studies demonstrating that activated NF-κB can result in protection of mitochondria in cancer cells from dysfunction leading to cell death.

Insights into the regulatory role of NF-κB in apoptosis come from findings related to its activation induced by TNFα. See Wang C Y, et al. (1996) Science 274:784–787; Wang C Y, et al. (1999) Mol Cell Biol 5923–5929; and LaCasse E, et al. (1998) Oncogene 3247–3529, which are herein incorporated by reference. TNFα stimulates apoptosis but the full extent of this stimulation in apoptosis is prevented by TNFα-induced activation of NF-κB. NF-κB activation occurs as a result of phosphorylation and degradation of NF-κB-associated proteins-IκBα and IκBβ (inhibitory κBs). Although the exact mechanism underlying the phosphorylation and degradation of the IκBs is incompletely understood, the phosphorylation can be initiated by IKK and phosphatidylinositol 3-kinase (PI 3-kinase) and modulated by ROS. See Kane L P, et al. (1999) Curr Biol 9:601–604; Romashkova J A and Makarov SS. (1999) Nature 401:86–90; Ozes O N, et al. (1999) Nature 401:82–85; Madrid LV, et al. (2000) Mol Cell Biol 20:1626–1638; Xie P, et al. (2000) J Biol Chem 275:24907–24914; Madrid L V, et al. (2001) J Biol Chem 276:18934–18940; Lepri E, et al. (2000) Cell Biochem Funct 18:201–208; Lin K I, et al. (1999) J Biol Chem 274:13650–13655; McDade T P, et al. (1999) J Surg Res 83:56–61; Wolf B B, et al. (2001) J Biol Chem 276:34244–34251; Flohe L, et al. (1997) Free Radic Biol Med 22:1115–1126, which are herein incorporated by reference. The phosphorylation of the IκB's leads to their transport to and rapid degradation by proteasomes. With IκB degradation, NF-κB translocates to the nucleus where it binds to promoter regions of target genes and activates them.

The mechanisms of the anti-apoptotic action of NF-κB are not fully understood. The known anti-apoptotic targets of activated NF-κB include the inhibitors of apoptosis (IAP) family of proteins, such as cIAP-1 and -2, and XIAP, as well as the anti-apoptotic Bcl-2 proteins.

As described herein, the effects of the polyphenolic compounds on mitochondrial dysfunction in pancreatic cancer cells incubated in the absence of serum of growth factors were independent from the effects on NF-κB activation. Since it was possible that in the presence of serum, at least one of the effects of the polyphenolic compounds could be through its effect on NF-κB. As provided in Example 7, the addition of serum to the incubation media caused an increase in NF-κB activation that was not inhibited by DPI, genistein, or trans-resveratrol alone, but was completely inhibited with the combination of DPI and either trans-resveratrol or genistein. The proteosome inhibitor, MG-132, blocks NF-κB activation in both cell lines and causes a small increase in caspase-3 activity. Additionally, trans-resveratrol in combination with MG-132 alone or MG-132 plus DPI increased apoptosis to a greater degree than that observed with MG-132 alone or MG-132 plus DPI, thereby indicating that inhibition of NF-κB sensitizes the cancer cells to apoptosis caused by trans-resveratrol.

Therefore, the present invention provides a method of preventing or inhibiting NF-κB activation in a cell comprising administering to the cell DPI and at least one polyphenolic compound or MG-132 and at least one polyphenolic compound or MG-132 and DPI. Since DPI is an antioxidant and MG-132 is a proteosomal inhibitor, the present invention provides a method of preventing or inhibiting NF-κB activation in a cell comprising administering to the cell an antioxidant, a proteosomal inhibitor, or both and at least one polyphenolic compound. The present invention also provides a method of making a cancer cell susceptible to apoptosis induced by a polyphenolic compound comprising inhibiting NF-κB activity in the cell.

E. PI 3-Kinase

Next, the possibility that phosphatidylinositol 3-kinase (PI 3-kinase) and Akt/PKB mediate the effects of serum on NF-κB; and that the effects of the polyphenols on NF-κB activation are due, at least in part, to an ability to inhibit PI 3-kinase were studied. The PI 3-kinase signaling system was used because it is an important mediator of responses to growth factors and because there is evidence that polyphenolic compounds such as quercetin and genistein inhibit PI 3-kinase and/or Akt/PKB. Of note, one commonly used inhibitor of PI 3-kinase is LY294002 (Calbiochem, San Diego, Calif.), a derivative of quercetin. Also, there are some suggestions for a role of ROS in activation of PI 3-kinase. Finally, and most importantly, there are several publications indicating that one of the effects of PI 3-kinase signaling is the activation of NF-κB. See Kane L P, et al. (1999) Nature 401:86–99; Ozes O N, et al. (1999) Nature 401:82–85; Madrid LV, et al. (2000) Mol Cell Biol 20:1626–1638; Xie P, et al. (2000) J Biol Chem 275: 24907–24914; and Madrid L V, et al. (2001) J Biol Chem 276:18934–18940, which are herein incorporated by reference.

PI 3-kinase is an important signaling system that is activated by growth factors and G protein-coupled receptors that have been determined to regulate various cellular processes including proliferation, survival, inflammation and metabolism. See Katada T, et al. (1999) Chem Phys Lipids 98:79–86; and Leevers S J, et al. (1999) Curr Opin Cell Biol 11:219–225, which are herein incorporated by reference. The activation of PT 3-kinase results in an increase in D-3 phosphorylated phosphoinositides such as phosphatidylinositol-3 phosphate, phosphatidylinositol-3,4 bisphosphate and phosphatidylinositol-3,4,5 trisphosphate.

The PI 3-kinase that is stimulated by tyrosine kinase activating receptors is relevant to the present application. This PI 3-kinase is structurally characterized as a heterodimer consisting of a 110-kD catalytic subunit (p110-α, β or -γ) and an 85-kD regulatory subunit (p85). Stimulation of tyrosine kinase activating receptors by extracellular signals, i.e. insulin and insulin-related growth factors results in phosphorylation of the receptor or receptor associated adapter proteins. The phosphorylated receptor or adapter proteins then bind to regulatory p85, which, in turn, activates catalytic p 110. Of particular note, although structurally different, there is no difference in function between the isotypes of p110 described to date. Furthermore, each isotype is inhibited specifically by wortmannin and LY294002. LY294002 acts on an ATP-binding site while wortmannin blocks the catalytic activity of PI 3-kinase. See Balla T (2001) Curr Pharm Des 7:475–507, which is herein incorporated by reference.

As indicated above, with activation of PI 3-kinase, there is formation of D-3 phosphorylated phosphoinositides. These phospholipids then activate a protein kinase called Akt or protein kinase B (Akt/PKB). See Kandel ES and Hay N (1999) Exp Cell Res 253:210–229, which is herein incorporated by reference. Many of the known effects of PI 3-kinase are mediated through Akt/PKB.

As provided in Example 8, serum increases the activated phosphorylated state of Akt/PKB, and LY294002 prevents the serum activation. Additionally, genistein attenuated serum-induced Akt phosphorylation/activation. The combination of LY294002 and DPI inhibits NF-κB activation in a manner similar to the combination of a polyphenolic compound and DPI. The combination a ROS inhibitor and the PI 3-kinase inhibitor, LY294002, inhibit NF-κB activation. As indicated above, inhibition of NF-κB activation can, in turn, sensitize the cancer cell to apoptosis.

Therefore, the present invention provides a preventing, inhibiting, or attenuating the activation of Akt/PKB in a cell comprising administering to the cell at least one polyphenolic compound or a ROS inhibitor and a PI 3-kinase inhibitor, or at least one polyphenolic compound and an inhibitor of NADPH oxidase or inhibitor of ROS formation.

Thus, the present invention provides methods of treating, preventing, or inhibiting cancer in a subject comprising administering to the subject at least one polyphenolic compound. The methods of the present invention may further comprise one or more of the following:

1. Administering a ROS inhibitor;
2. Administering a PI 3-kinase inhibitor;
3. Administering a NADPH oxidase inhibitor;
4. Preventing or inhibiting NF-κB activation;
5. Inducing apoptosis;
6. Inducing caspase-3 activation;
7. Inducing mitochondrial cytochrome c release;
8. Inducing dissipation of mitochondrial polarity; and
9. Activating mitochondrial PTP; and
10. Activating PARP.

In accordance with the present invention, at least one polyphenolic compound may be administered in a therapeutically effective amount to a mammal such as a human. A therapeutically effective amount may be readily determined by standard methods known in the art.

An effective amount of a polyphenolic compound is an amount that treats, prevents, or inhibits cancer or tumor growth as compared to a control using methods known in the art. An effective amount of a polyphenolic compound may also mean an amount that induces apoptosis in a cancer cell as compared to a control using methods known in the art. The dosages to be administered can be determined by one of ordinary skill in the art depending on the clinical severity of the disease, the age and weight of the subject, or the exposure of the subject to carcinogens and neoplastic conditions. Preferred effective amounts of the compounds of the invention ranges from about 1 to about 2400 mg/kg body weight, preferably about 10 to about 1000 mg/kg body weight, and more preferably about 10 to about 500 mg/kg body weight. Preferred topical concentrations include about 0.1% to about 10% in a formulated salve.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a compound or composition of the present invention can include a single treatment or, preferably, can include a series of treatments.

In a preferred example, a subject is treated with a compound of the invention in the range of between about 1 to about 2400 mg/kg body weight, at least one time per week for between about 1 to about 24 weeks, and preferably between about 1 to about 10 weeks. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given compound. Administration of prodrugs may be dosed at weight levels that are chemically equivalent to the weight levels of the fully active forms.

The polyphenolic compounds of the invention can be incorporated into pharmaceutical compositions suitable for administration. Pharmaceutical compositions of this invention comprise a therapeutically effective amount of a polyphenolic compound, and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art.

Except insofar as any conventional media or agent is incompatible with the active compound, use thereof in the compositions is contemplated. Supplementary active compounds can also be incorporated into the compositions. Supplementary active compounds include ROS inhibitors such as N-acetylcysteine, vitamins C, A, and E, beta-carotene, allopurinol, carvediol, coenzyme Q, Tiron, DPI, and any other antioxidant or inhibitor of ROS.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a polyphenolic compound is dissolved in an aqueous solution of an organic or inorganic acid, such as 0.3M solution of succinic acid or citric acid. If a soluble salt form is not available, the compound may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, the polyphenolic compound of the present invention is dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may comprise formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating at least one polyphenolic compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., comprising conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The polyphenolic compounds of the present invention may be prepared using reaction routes, synthesis schemes and techniques available in the art using starting materials that are readily available.

The following examples are intended to illustrate but not to limit the invention.

EXAMPLE 1

Pancreatic Cancer Growth Assay

To determine the effect of a polyphenolic compound on pancreatic cancer cell growth, the following assay using a nude mouse model was conducted. Specifically, the effect of quercetin was tested in a nude mouse model of pancreatic cancer using the highly malignant pancreatic cancer cell line, Mia PACA-2.

Tumor induction in nude mice was performed as described by Hotz HC, et al. (2001) Pancreas 22:113–121, which is herein incorporated by reference. For subcutaneous tumor formation, 1×10⁷ Mia PACA-2 tumor cells were subcutaneously injected in the medio-dorsal region of a nude mouse. After 4 weeks a small tumor fragment, about 1 mm in diameter, was removed from the subcutaneous tumor and transplanted into the pancreatic tail of mice of two study groups. Ten days after tumor transplantation, treatment with or without quercetin was initiated. The treated animals received daily intraperitoneal injections of 1.3 mg quercetin dissolved in DMSO; the control group received DMSO only by intraperitoneal injection. The animals were sacrificed once clinical tumor signs including severe cachexia ascites with abdominal distension or heavy tumor burden, larger than 1.5 cm, became apparent. Tumor volume was calculated as described by Hotz H C, et al. (2001) as 0.5×length× width×depth. Metastatic tumor spread was determined macroscopically at autopsy in all thoracic, abdominal, retroperitoneal and pelvic organs. All macroscopic suspicious lesions were further confirmed as tumor dissemination by microscopic analysis. Each value in the metastatic score represented a different organ of metastatic tumor spread.

As indicated in Table I, the quercetin treatment had multiple effects on the in vivo growth of the tumor.

TABLE 1

Effect of Treatment with Quercetin on Tumor Progression In Vivo[1]

| Parameters of cancer development | Control | Quercetin |
| --- | --- | --- |
| Survival, days | 66.60 ± 3.20 | 75.00 ± 2.50* |
| Tumor volume, cm³ | 5.76 ± 0.92 | 1.56 ± 0.27* |
| Number of metastatic sites | 4.40 ± 0.90 | 0.62 ± 0.26* |
| Percentage of apoptosis | 3.30 ± 0.60 | 7.10 ± 1.00* |

[1]Survival in control animals was measured as the number of days after transplantation until the animal died or appeared severely ill. Survival in the quecetin-treated animals was measured as the number of days after transplantation until the animal appeared ill from abdominal distension. The distension was due to dilation of the small and large bowels. The values represent means ± SE n = 8.-*p < 0.05 compared to untreated animals.

Additionally, the mean number of organs with metastatic lesions was 4.4 in control animals as compared to the 0.6 in quercetin-treated animals. Therefore, quercetin treatment prevents metastatic cancer lesions. Furthermore, quercetin treatment significantly decreased the growth of the primary tumor.

EXAMPLE 2

Effects of Serum and Growth Factors

To determine the effect of serum in cancer cells, the following assay was conducted. Mia PACA-2 pancreatic cancer cells were cultured for 72 hours in the absence and presence of serum (15% FBS) or 100 ng/ml insulin growth factor-1 (IGF-1). Dichloroflyorescein diocetate (DCF-DA) was used to label the cells. Intracellular $H_2O_2$ was measured by flow cytometry of DCF-labeled cells.

Intracellular ROS was measured using oxidation-sensitive cell-permeable fluorescent probe, dichlorofluorescein diacetate (DCF-DA) to measure $H_2O_2$. See Royall J A, and Ischiropoulos H. (1993) Arch. Biochem. Biophys. 302:348–355. To measure ROS, cells were collected after incubation, washed with PBS, and incubated for 15 minutes with 8 mM DCF-DA. Samples were analyzed by flow cytometry. The amount of DCF-DA fluorescence correlated with the amount of ROS in the cells To determine the effects of serum, IGF-1, polyphenols and inhibitors of ROS on ROS production in cancer cells, the following assay was conducted. Mia PACA-2 cells were cultured for 72 hours in the presence of serum or IGF-1 with or without antioxidants, intracellular superoxide scavenger tiron (10 mM) or NADPH oxidase inhibitor, diphenylene iodonium (DPI, 15 µM) and trans-resveratrol (100 µM), genistein (100 µM), or a combination of polyphenolic compounds and antioxidants. Intracellular $H_2O_2$ was measured by flow cytometry of DCF-labeled cells.

Mia PACA-2 cells and BSp73AS cells were cultured in Dulbecco's Modified Eagle's Medium supplemented with 10% heat inactivated FBS, penicillin G (100 U/ml) and streptomycin (100 mg/ml) in a humidified atmosphere comprising 5% (v/v) $CO_2$. When the cells were 90% confluent they were detached, washed with alternating centrifugation and resuspension, plated and incubated in the same media with or without FBS or IGF-1 and with or without a given polyphenolic compound and with or without a given ROS inhibitor.

Figure 2:
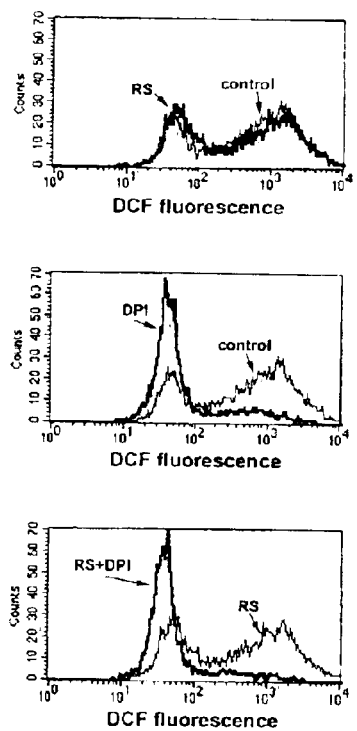
FIG. 2A shows the results of intracellular $H_2O_2$ measured by flow cytometry of DCF-labeled cells. DPI=diphenylene iodonium; RS=trans-resveratrol; Gen=genistein.
FIG. 2B shows the percentage of cells with high DCF fluorescence. Values are means±SE (n=3). $*p<0.05$ compared to control cells. DPI=diphenylene iodonium; RS=trans-resveratrol; Gen=genistein.
Figure 2:
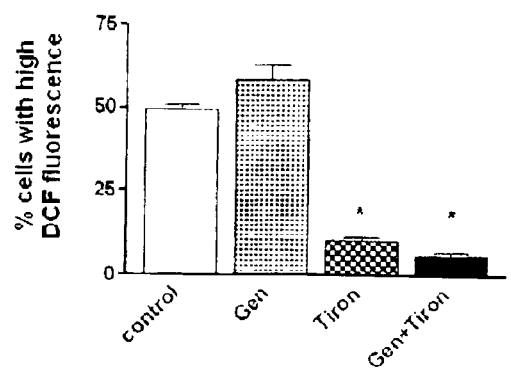

As shown in FIG. 1, the presence of serum and insulin growth factor-1 (IGF-1) increases the percentage of cells with a high DCF fluorescence value. As shown in FIG. 2, antioxidants, but not trans-resveratrol and genistein inhibit production of ROS in Mia PACA-2 pancreatic cancer cells. As illustrated in FIG. 2A, the addition of agents that decrease the production of ROS caused a decrease in the percentage of cells that were highly fluorescent. Additionally, trans-resveratrol and genistein caused small increase in ROS production, which were prevented by DPI.

EXAMPLE 3

Apoptosis Assays

I. POLYPHENOLIC COMPOUND ALONE

In order to determine the mechanism of the suppressive effects of quercetin on the growth of the pancreatic cancer, apoptosis in the primary tumors using the TUNEL assay was conducted. See Gukovskaya AS, et al. (1997) Clin Invest 100:1853–1862; Gukovskaya AS, et al. (1996) Gastroenterology 110:875–884; and Sandoval D, et al. (1996) Gastroenterology 111:1081–1091, which are herein incorporated by reference. Specifically, 3 µm tissue section were deparaffinized and rehydrated through a graded series of ethanol and redistilled water. Tissue sections were refixed in 4% paraformaldehyde for 15 minutes at room temperature and then incubated with proteinase K (20 µg/ml in 10 mM Tirs/HCL, pH 7.4–8.0) for 15 minutes at 37° C. DNA breaks were then labeled with terminal deoxytransferase (TdT) and biotinylated deoxyUTP. Staining without TdT enzyme or the biotinylated substrate were used as negative controls. For positive controls, slides were treated with DNase I. Measurements were made by light microscpy observations and values calculated as the percentage of cells positively stained as a percentage of the total number of cells.

Also as shown in Table I above, there was a significant increase in the percentage of cells undergoing apoptosis in the quercetin-treated animals as compared to the control animals. In contrast to the effect of the quercetin treatment on apoptosis in the tumor tissue, there was no increase in apoptosis detected by the TUNEL assay in normal tissues (data not shown), thereby indicating that the effect of quercetin on apoptosis is tumor tissue specific.

To confirm the apoptosis in vivo results, the effects of quercetin, rutin, and trans-resveratrol in other apoptosis assays in Mia PACA-2 cells and BSp73AS cells in culture were conducted. BSp73AS cells are derived from a rat pancreatic carcinoma and both Mia PACA-2 and BSp73AS cells have mutated p53 and express K-ras. Human pancreatic carcinoma cell line Mia PACA-2 and rat pancreatic carcinoma BSp73AS were cultured in Dulbecco's Modified Eagle's Medium supplemented with 10% heat inactivated FBS, penicillin G (100 U/ml) and streptomycin (100 mg/ml) in a humidified atmosphere comprising 5% (v/v) $CO_2$. When cells were 90% confluent they were detached, washed with alternating centrifugation and resuspension, plated and incubated in the same media without FBS and with the indicated concentrations of polyphenolic compounds or vehicle for up to 96 hours. Oligonucleotide DNA fragmentation, annexin staining, and PARP proteolysis assays were conducted as follows:

A. Oligonucleotide DNA Fragmentation

BSp73AS pancreatic cancer cells were cultured for 6 hours in the presence or absence of 100 $\mu$M of rutin, quercetin, or trans-resveratrol. DNA was isolated as described by Gukovskaya AS, et al. (1997) Clin Invest 100: 1853–1862, which is herein incorporated by reference. Briefly, pancreatic cancer cells growing on plates were removed by treatment with trypsin, collected by centrifugation and lysed by resuspension in a buffer comprising 10 mM Tris/HCl (pH 8.0) 10 mM NaCl, 10 mM EDTA, 300 $\mu$g/ml proteinase K and 1% SDS. Cell lysates were incubated overnight at 45° C.; and DNA was purified by phenol/chloroform extraction (1:1 v/v), precipitated overnight at 20° C. with 0.3 M sodium acetate and collected by centrifugation at 15,000 g for 15 minutes at 4° C. The pellet comprising RNA and DNA was resuspended in TE buffer (10 mM Tris/HCl (pH 8.0), 1.0 mM EDTA) and treated subsequently with RNase (200 $\mu$g/ml) for 2 hours at room temperature, followed by an incubation overnight with proteinase K (200 $\mu$g/ml) at 45° C. Finally, the mixture was re-extracted with phenol/chloroform and chloroform, precipitated with ethanol and resuspended in TE buffer. DNA fragments were separated electrophoretically on 1.8% agarose gel comprising 0.5 $\mu$g/ml ethidium bromide in 0.5×TBE buffer (TBE: 89 mM Tris base, 89 mM boric acid and 2 mM EDTA). The experiment was repeated twice with similar results.

B. Annexin Staining

Mia PACA-2 cells were cultured for 72 hours in the presence of 0, 12, 24, 50, and 100 $\mu$M rutin, quercetin, or trans-resveratrol. About 1×10$^6$ cells as determined with a hemocytometer were analyzed for annexin-V binding using an Annexin V-FLUOS Staining Kit (Boehringer Mannheim, Germany). Briefly, cells were washed twice with PBS and incubated for 10 minutes at room temperature with fluorescein isothiocyanate (FITC)-conjugated, annexin-V reagent (20 $\mu$g/ml) and propidium iodide (50 $\mu$g/ml). Cells were analyzed on a FACScan flow cytometer (Becton Dickinson Immunocytometry System, San Jose, Calif.) equipped with a 15 nW air-cooled 488 nm argon-ion laser. Annexin-V positive and propidium iodide negative cells were considered as apoptotic.

C. PARP Proteolysis

BSp73AS cells were cultured for 6 hours and Mia PACA-2 cells were cultured for 24 hours in the presence or absence of 100 $\mu$M of each rutin, quercetin or trans-resveratrol and with or without 50 $\mu$M of each K-VAD FMK(K-VAD). The cells were washed twice with PBS and lysed by incubating for 20 minutes at 4° C. in lysis buffer comprising 0.15 M NaCl, 50 mM Tris (pH 7.2), 1% deoxycholic acid (wt/vol), 1% Triton X-100 (wt/vol), 0.1% SHS (wt/vol) and 1 mM PMSF, as well as 5 $\mu$g/ml each of protease inhibitors, pepstatin, leupeptin, chymostatin, antipain, and aprotinin. Then the cell lysates were centrifuged for 20 minutes at 15,000 g at 4° C. The supernatants were separated by 4–20% SDS-PAGE for 2 hours at 120 V using precast Tris-glycine gels and a Mini-Cell gel apparatus (Novex, San Diego, Calif.). Separated proteins were electrophoretically transferred to a nitrocellulose membrane for 2 hours at 30 V using a Novex Blot Module (Novex, San Diego, Calif.). Nonspecific binding was blocked by 1 hour incubation of nitrocellulose membranes in 5% (wt/vol) nonfat dry milk in Tris-buffered saline (TBS; pH 7.5). Blots were then incubated overnight at 4° C. with rabbit polyclonal antibody against poly (ADP-ribose) polymerase (PARP) (Santa Cruz Biotechnology, Santa Cruz, Calif.) (1;3,000) in an antibody buffer comprising (1% (wt/vol) non-fat dry milk in TTBS (0.05% vol/vol) Tween-20 in TBS), washed 3 times with TTBS and finally incubated for 1 hour with a peroxidase-labeled secondary antibody in the antibody buffer. Blots were developed for visualization using ECL detection kit. To test for equal protein loading, the blots were stripped and re-probed with an antibody against tubulin. When processing of a protein was measured, a decrease in unprocessed full-length form was measured concomitantly with the increase in the cleaved, active form. The experiment was repeated 3 times with similar results.

Figure 3:
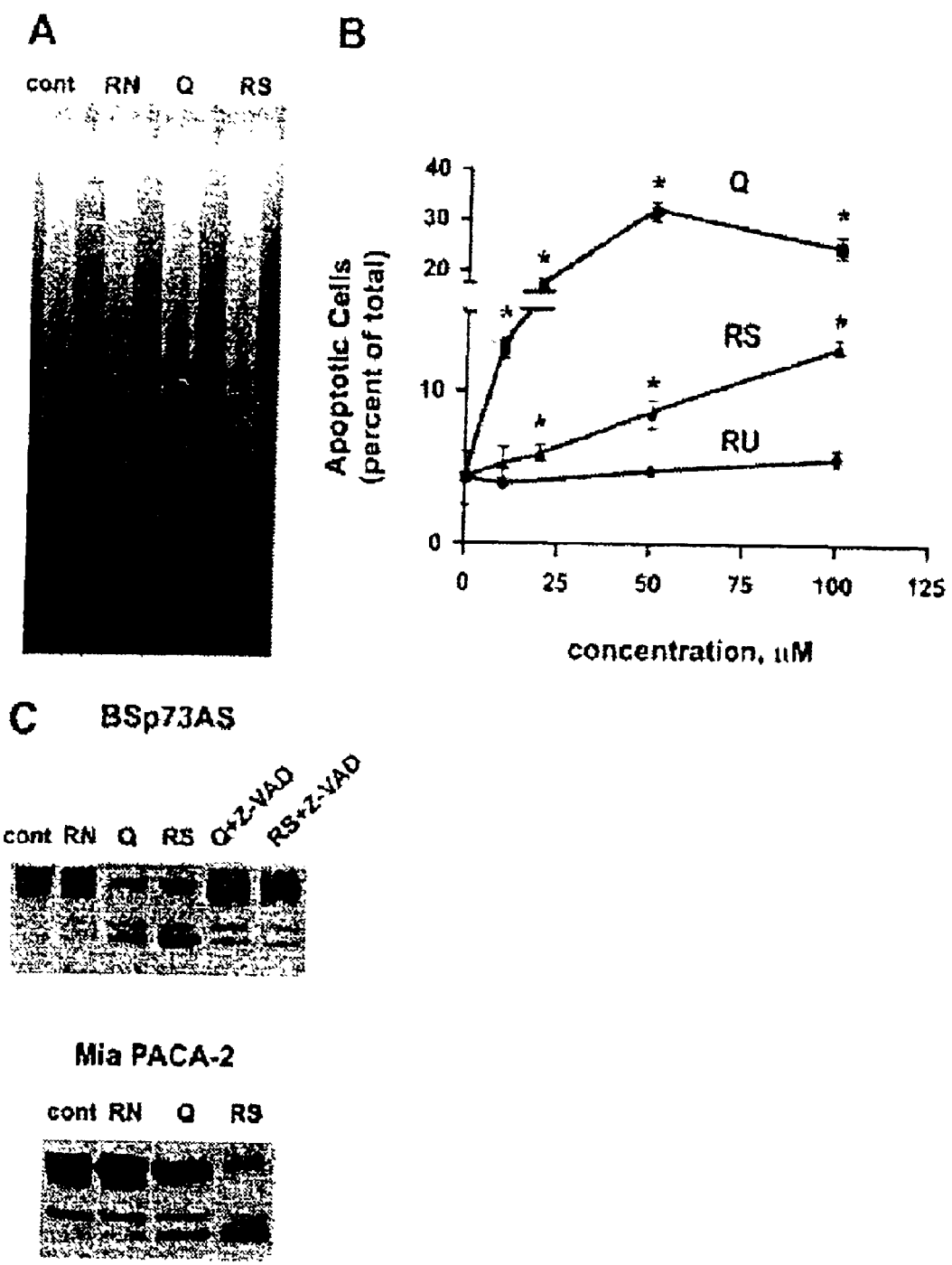
FIG. 3A is a gel eletrophoresis that shows that quercetin and trans-resveratrol, but not rutin, caused an increase in oligonucleosomal DNA fragmentation. RN=rutin, Q=quercetin, RS=trans-resveratrol.
FIG. 3B is a graph showing that quercetin is more potent in causing apoptosis than trans-resveratrol. The values represent means±SE (n=3). $*p<0.05$ compared to control cells. RN=rutin, Q=quercetin, RS=trans-resveratrol.
FIG. 3C are Western blots that illustrate that poly(ADP-ribose) polymerase (PARP) was cleaved in cell lines treated with quercetin and trans-resveratrol, but not rutin. RN=rutin, Q=quercetin, RS=trans-resveratrol.

As indicated in FIGS. 3A and 3B, quercetin and trans-resveratrol, but not rutin, caused an increase in oligonucleosomal DNA fragmentation, a unique characteristic of apoptosis, as well as increase annexin staining. Annexin staining is a measure of externalization of phosphatidylserine to the outer plasma membrane leaflet representing another unique characteristic of apoptosis. The dose-response evaluation in FIG. 3B indicates that quercetin is more potent in causing apoptosis than trans-resveratrol. Finally, FIG. 3C illustrates that a protein target of caspases-3 activation, PARP, was cleaved to its activated form in cell lines treated with quercetin and trans-resveratrol, but not rutin. The cleavage did not occur in the presence of the specific caspase inhibitor, Z-VAD. These effects of quercetin and trans-resveratrol on apoptosis occurred independent of the presence of serum in the incubation media.

Therefore, quercetin and trans-resveratrol activate apoptosis in pancreatic cancer cells and indicate that the beneficial effect of quercetin in vivo is due to the ability to cause apoptosis.

II. COMBINATIONS

To evaluate the effects of polyphenolic compounds alone and in combination with ROS inhibitors on apoptosis in pancreatic cancer cells, the following assays were conducted.

Mia PACA-2 cells were cultured for 72 hours in the presence of serum with or without 15 $\mu$M DPI, 10 mM Tiron, 100 $\mu$M genistein, 100 $\mu$M or 50 $\mu$M trans-resveratrol, or a combination thereof. Oligonucleosomal DNA fragmentation was measured in cell lysates by cell death ELISA.

Mia PACA-2 cells were cultured for 72 hours in the presence of serum with or without 10 mM Tiron, 100 $\mu$M trans-resveratrol, or a combination thereof. Phosphatidylserine externalization was measured by flow cytometry in cells stained with Annexin V and propidium iodide (PI). Cells positive for Annexin V (AnV) and negative for PI were considered apoptotic.

Annexin staining was conducted as described above. Cells were collected, washed with PBS, and centrifuged for 10 min at 200×g. DNA fragmentation was determined using Cell Death Detection ELISA Plus kit (Roche Molecular Biochemicals).

Figure 4:
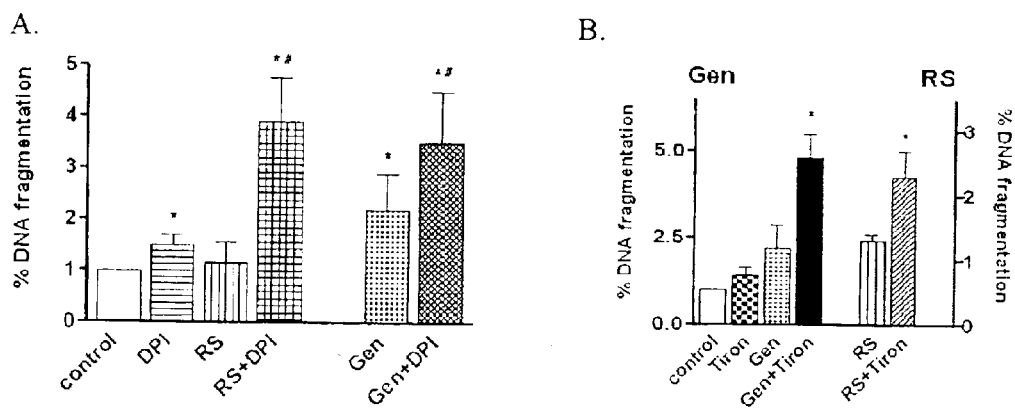
FIGS. 4A and 4B show that the combination of inhibitors of production of ROS and polyphenolic compounds cause oligonucleosomal DNA fragmentation in Mia PACA-2 pancreatic cancer cells. DPI=diphenylene iodonium; RS=trans-resveratrol; Gen=genistein. Values are means±SE (n=5). $*p<0.05$ compared to control cells. $\#p<0.05$ compared to cells treated with polyphenols only, or antioxidants only.
Figure 5:
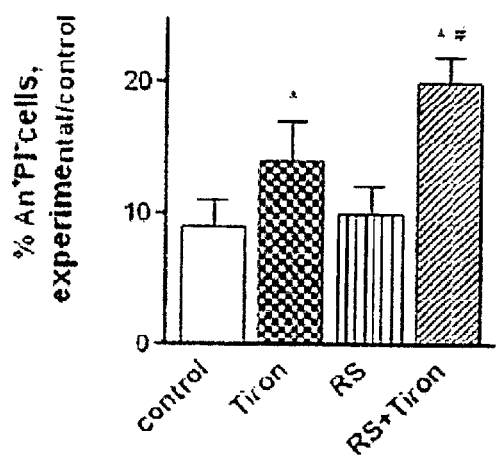
FIG. 5 shows the effects of inhibition of ROS and trans-resveratrol on Annexin V staining in Mia PACA-2 pancreatic cancer cells. PI=propidium iodide; AnV= Annexin V; RS=trans-resveratrol; Gen=genistein. Values are means±SE (n=3) $*p<0.05$ compared to control cells. $\#p<0.05$ compared to cells treated with resveratrol only, or tiron only.

As shown in FIG. 4, the combination of ROS inhibitors and polyphenolic compounds caused oligonucleosomal DNA fragmentation in Mia PACA-2 pancreatic cancer cells. Specifically, at the concentrations used, DPI, trans-resveratrol, and genistein had either no or small effects on oligonucleosomal DNA fragmentation. However, the combination of DPI with either polyphenolic compound resulted in synergistic increases in DNA fragmentation. These results were confirmed by the similar results obtained by the Annexin V staining which are illustrated in FIG. 5.

EXAMPLE 4

Caspase-3 Assays

I. POLYPHENOLIC COMPOUND ALONE

In order to determine the effect polyphenolic compounds have on caspase-3 activity, the following assay was conducted. BSp73AS cells were culture in the absence of serum or growth factors for 24 hours in 0, 10, 20, and 50 $\mu$M of trans-resveratrol and Mia PACA-2 -cells were cultured for 72 hours in the presences of 0, 10, 20, and 50 $\mu$M of tran-resveratrol. Cell lysates were then prepared and 50 $\mu$g protein aliquots were loaded per lane and blotted with rabbit polyclonal antibody against caspase-3 (Santa Cruz Biotechnology, Santa Cruz, Calif.). The experiment was repeated 3 times with similar results.

To determine whether a polyphenolic compound activates caspase-3 activity in a time-dependent manner, the following assay was conducted. BSp73AS cells were cultured for 0, 1, 3, and 6 hours and Mia PACA-2 cells were cultured in the absence of serum or growth factors for 0, 1, 4, 6, and 24 hours in the presence of 100 $\mu$M or quercetin, trans-resveratrol, rutin, or control. Caspase-3 activity was measured in cell lysates with a fluorogenic assay using DEVD-AMC as a substrate. The results were normalized to the DEVDase activity in untreated cells.

To determine whether quercetin activates caspase-3 activity in a dose-dependent manner, the following assay was conducted. Cells were cultured for 6 hours in the absence of serum or growth factors in the presence of 0, 10, 20, 50, and 100 $\mu$M of quercetin. Caspase-3 activity was measured in cell lysates with a fluorogenic assay using DEVD-AMC as a substrate. The results were normalized to the DEVDase activity in untreated cells.

Figure 6:
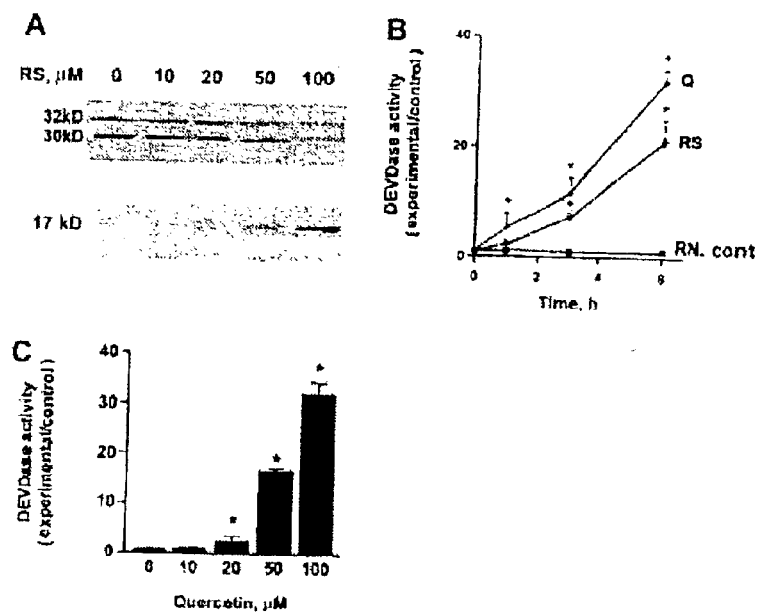
FIG. 6A is a Western blot showing that trans-resveratrol converts caspase-3 into the active form in BSp73AS cells.
FIG. 6B shows the results of a fluorogenic assay that confirms that trans-resveratrol and quercetin activate caspase-3 in a time dependent manner in BSp73AS cells. The values represent means±SE (n=3). $*p<0.05$ compared to control cells. RN=rutin, Q=quercetin, RS=trans-resveratrol.
FIG. 6C shows the results of a fluorogenic assay that confirms that quercetin activates caspase-3 in a dose dependent manner in BSp73AS cells. The values represent means±SE (n=3). $*p<0.05$ compared to control cells. RN=rutin, Q=quercetin, RS=trans-resveratrol.
Figure 7:
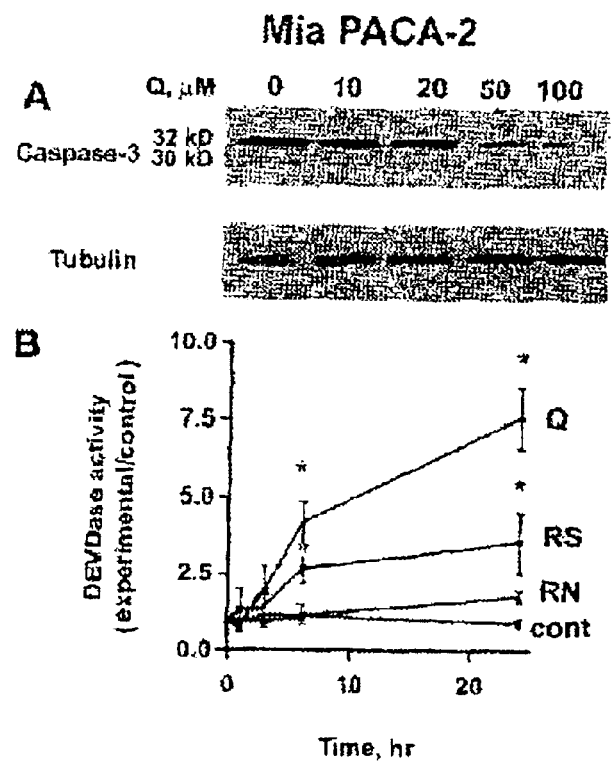
FIG. 7A is a Western blot showing that quercetin converts caspase-3 into the active form in Mia PACA-2 cells.
FIG. 7B shows the results of a fluorogenic assay that confirms that trans-resveratrol and quercetin activate caspase-3 in a time dependent manner in Mia PACA-2 cells. The values represent means±SE (n=3). $*p<0.05$ compared to control cells. RN=rutin, Q=quercetin, RS=trans-resveratrol.

As provided in FIGS. 6A and 7A, both quercetin and trans-resveratrol convert caspase-3 from its inactive form (32 kDa doublet) to its active form (17 kDa) as illustrated by a decrease in the inactive form and an increase in the active form using Western blot analysis and an antibody that recognizes both forms. The results show a dose dependency with effects occurring with as little as 20 $\mu$M for both compounds. FIGS. 6B, 6C, and 7B show that both quercetin and trans-resveratrol, but not rutin, caused caspase-3 activation as provided in the specific fluorogenic assay for caspase-3. As shown in FIGS. 6A, 6C, and 7A, the effects on caspase-3 activity were dose dependent and as shown in FIGS. 6B and 7B, the effects on caspase-3 activity were time dependent. In particular, the results show that effects of quercetin and trans-resveratrol on apoptosis were more rapid in BSp73AS cells as compared to Mia PACA-2 cells.

II. COMBINATIONS

To determine the role of caspases in the effects of combinations of agents on apoptosis, the effects of caspase-3 activity (DEVDase activity) as well as the effect of the broad spectrum caspase inhibitor, Z-VAD, on apoptosis was measured. Specifically, Mia PACA-2 cells were cultured for 72 hours in the presence of serum with or without 100 $\mu$M Z-VAD, 15 $\mu$M DPI, 100 $\mu$M trans-resveratrol, 100 $\mu$M genistein, a combination of trans-resveratrol and DPI, and a combination of genistein and DPI. DEVDase activity was measured in whole cell lysates with a fluorimetric assay. DNA fragmentation was measured in cell lysates by cell death ELISA.

The ELISA assay for DNA fragmentation was conducted as described above. A fluorimetric assay for caspase-3 activity was conducted. Specifically, cells were collected, washed with ice-cold PBS and resuspended in lysis buffer comprising 0.5% Nonidet P-40 or manufactured by the name IGEPAL CA-630, 0.5 mM EDTA, 150 mM NaCl and 50 mM Tris at pH 7.5. Cell lysates were placed for 30 minutes on a rotator at 4° C. and then centrifuged for 15 minutes at 15,000 g. Cytosolic protein extracts (supernatants) were collected, protein concentrations were determined and the extracts were aliquoted and stored at −80° C. Enzyme assays were carried out at 37° C. in a buffer comprising 25 mM HEPES (pH 7.5), 10% sucrose, 0.1% CHAPS and 10 mM DTT with 800 g cytosolic protein and 20 $\mu$M of specific fluorogenic substrate. For capsase-3, the substrate was z-DEVD. Cleavage of the caspase substrate releases 7-amino-4-methylcoumarin (AMC), which emits a fluorescent signal with excitation at 38 run and emission at 440 nm. The reaction was started by addition of caspase-3 substrate, the readings were taken at 0, 60, 90, and 120 minutes. Fluorescence was calibrated using a standard curve for AMC. The data were expressed as mol AMC/mg protein/min.

Figure 8:
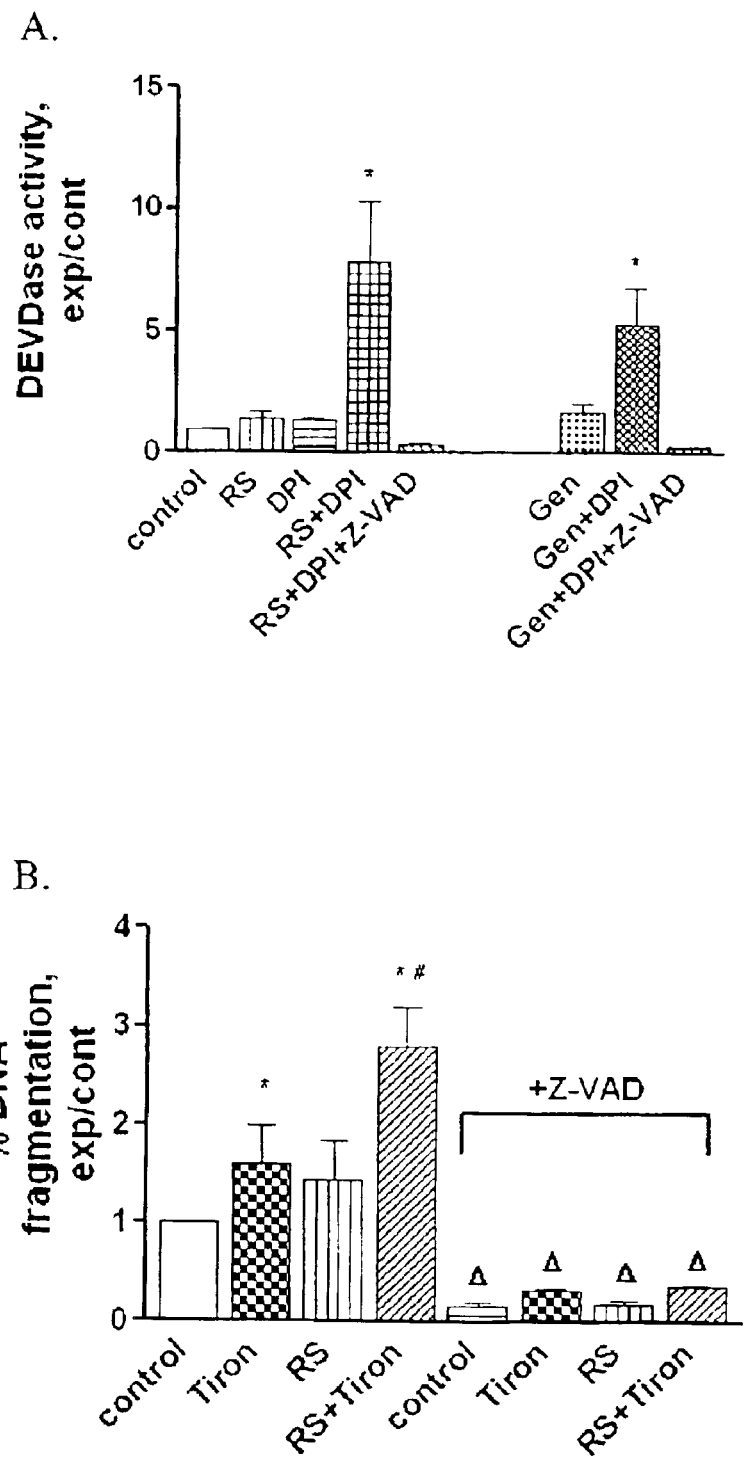
FIG. 8A shows the results of a fluorimetric assay providing that Tiron, polyphenolic compounds and a caspase inhibitor have an effect on caspase-3 activity in Mia PACA-2 pancreatic cancer cells. Z-VAD=z-VAD.fmk; DPI= diphenylene iodonium; RS=trans-resveratrol; Gen= genistein. Values are means±SE (n=3). $*p<0.05$ compared to control cells or cells treated with DPI only or polyphenolic compounds only. Values are means±SE (n=5).
FIG. 8B shows that Tiron, polyphenolic compounds and a caspase inhibitor have an effect on oligonucleosomal DNA fragmentation in Mia PACA-2 pancreatic cancer cells. $*p<0.05$ compared to control cells. $\#p<0.05$ compared to cells treated with polyphenols only, or antioxidants only. $\Delta p<0.05$ compared to the values obtained in the absence of Z-VAD.

As shown in FIG. 8, the caspase-3 activity and apoptosis are synergistically activated with a combination of an inhibitor of ROS production and a polyphenolic compound and Z-VAD inhibits apoptosis caused by the combinations.

EXAMPLE 5

Mitochondrial Assays

I. POLYPHENOLIC COMPOUND ALONE

In order to determine the effects polyphenolic compounds have on mitochondrial cytochrome c release and apoptosis, the following assay was conducted. BSp73AS cells were cultured for 6 hours and Mia PACA-2 cells were cultured in the absence of serum or growth factors for 24 hours in the absence or presence of 100 $\mu$M of each rutin, trans-resveratrol, genistein, or quercetin. Cells were washed twice with ice-cold PBS, pH 7.2 and resuspended in extraction buffer, about 500 $\mu$l, comprising 20 mM HEPES-KOH (pH 7.0), 10 mM KCl, 1 mM NaEGTA, 2 mM MgCl$_2$, 1 mM EDTA, 1 mM DTT, 250 mM sucrose, 1 mM PMSF and protease inhibitors cocktail as provided above. The lysate was incubated for 30 minutes on ice and then homogenized using a glass dounce (80 strokes). Nuclei were removed by centrifugation at 1,000 g for 10 minutes at 4° C. Supernatant was additionally centrifuged for 1 hour at 100,000 g and the resulting supernatant (cytosolic fraction) and pellet (mitochondrial fraction) were collected separately, subjected to SDS-PAGE, and Western blotting using an antibody against cytochrome c. The experiment was repeated twice with similar results.

In order to determine the effects polyphenolic compounds have on mitochondrial membrane potential, the retention of the dye 3,3'-dihexyloxacarbocyanine (DiOC$_6$(3)) was measured as described by Pastorino J G, et al. (1998) J Biol Chem 273:7770–7775, which is herein incorporated by reference. BSp73AS cells were cultured for 6 hours in the absence (control) or presence of 0, 12, 24, 50, and 100 $\mu$M quercetin and trans-resveratrol. The cells were loaded with 1 μM DiOC$_6$(3) during the last 30 minutes of treatment with a polyphenolic compound (or vehicle). The cells were then collected and pelleted by centrifugation. The supernatant was removed and the pellet was washed twice with PBS by alternate centrifugation and resuspension. The pellet was then lysed by addition of 1 ml of H$_2$O and homogenized. The concentration of DiOC$_6$(3) was read on a Perkin-Elmer LS-5 fluorescence spectrometer at 488 nm excitation and 500 nm emission. An aliquot of the cells was used for determining the DiOC$_6$(3) fluorescence that was retained by the cells.

Figure 9:
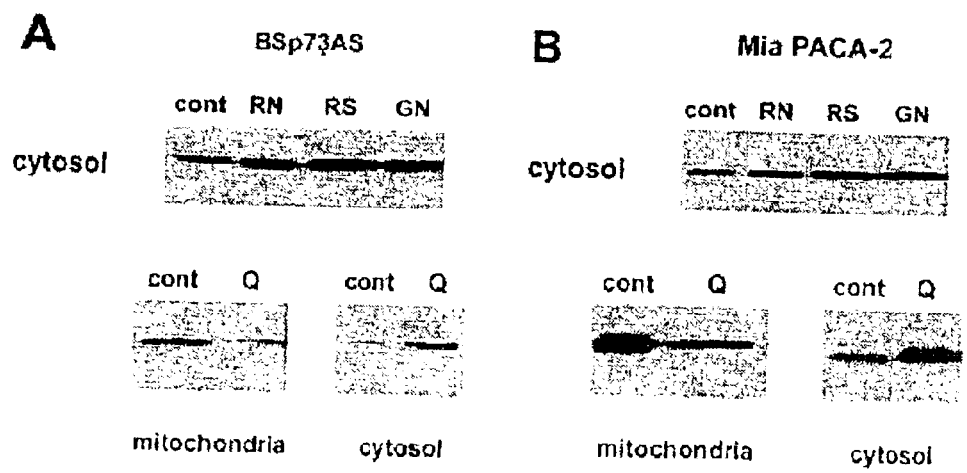
FIG. 9A is a Western blot showing that polyphenolic compounds stimulate mitochondrial release of cytochrome c in BSp73AS cells. RN=rutin, Q=quercetin, RS=trans-resveratrol, GN=genistein.
FIG. 9B is a Western blot showing that polyphenolic compounds stimulate mitochondrial release of cytochrome c in Mia PACA-2 cells. RN=rutin, Q=quercetin, RS=trans-resveratrol, GN=genistein.
Figure 10:
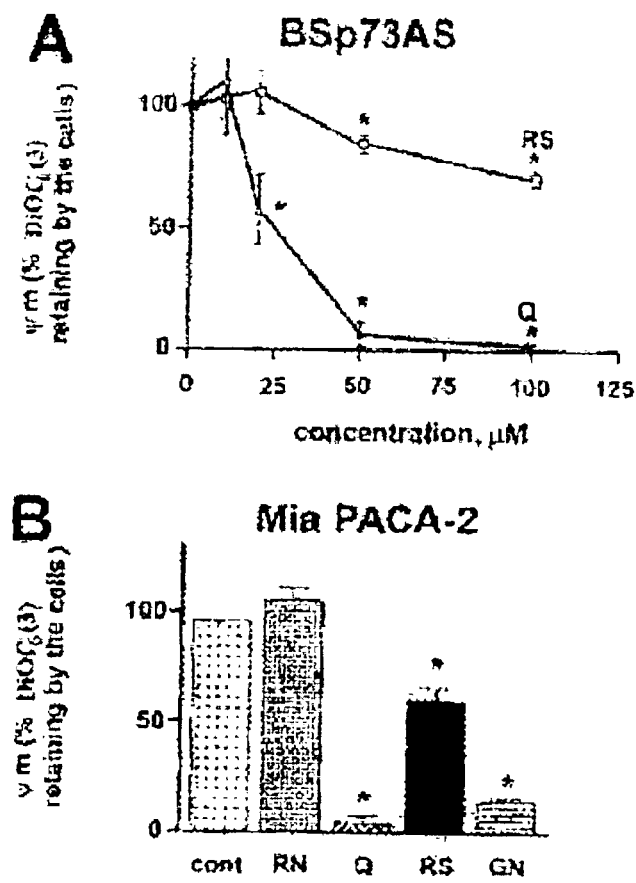
FIG. 10A shows that polyphenolic compounds induce depolarization of mitochondrial membrane potential in BSp73AS cells. The values represent means±SE (n=3). *p<0.05 compared to control cells. RN=rutin, Q=quercetin, RS=trans-resveratrol, GN=genistein.
FIG. 10B shows that polyphenolic compounds induce depolarization of mitochondrial membrane potential in Mia PACA-2 cells. The values represent means±SE (n=3). *p<0.05 compared to control cells. RN=rutin, Q=quercetin, RS=trans-resveratrol, GN=genistein.

As shown in FIG. 9, quercetin, trans-resveratrol and genistein, but not rutin, caused increases in cytosolic cytochrome c and decreases in mitochondrial cytochrome c As shown in FIG. 10, quercetin, trans-resveratrol, and genistein, but not rutin, caused dissipation of the mitochondrial membrane potential using a dye, DiOC$_6$(3), that is taken up in cells as a function of mitochondrial membrane potential. Because one mechanism of mitochondrial cytochrome c release involves opening of the mitochondrial permeability transition pore (PTP), which is associated with dissipation of the mitochondrial membrane potential, the results as shown in FIG. 9 and 10 suggest that the mechanism of action of the polyphenolic compounds on cytochrome c release and apoptosis is through the PTP.

II. COMBINATIONS

In order to determine the effects of the polyphenolic compounds alone and in combination with ROS inhibitors on mitochondrial membrane potential in the presence of serum, the following assay was performed.

Mia PACA-2 cells were cultured for 72 hours in the presence of serum and trans-resveratrol or genistein in the presence or absence of DPI or Tiron. Mitochondrial membrane potential was measured as described above.

Figure 11:
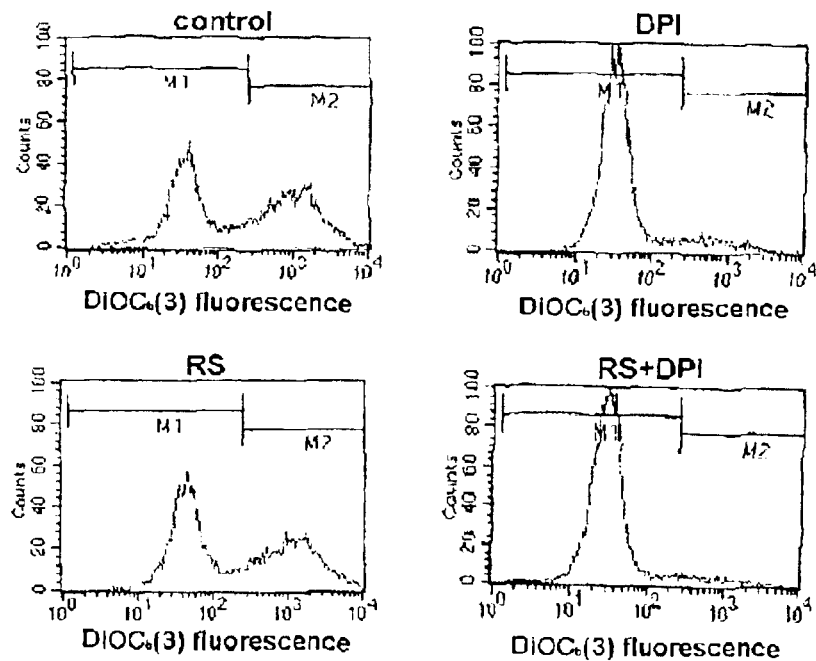
FIG. 11A shows the effects of DPI, and polyphenolic compounds on mitochondrial membrane potential in Mia PACA-2 pancreatic cancer cells. Changes in $\Delta\psi_m$ as measured by FACS® in cells labeled with $DiOC_6(3)$. Values are means±SE; (n=3).
FIG. 11B shows the percentage of cells with high $\Delta\psi_m$. Values are means±SE; (n=3).
Figure 11:
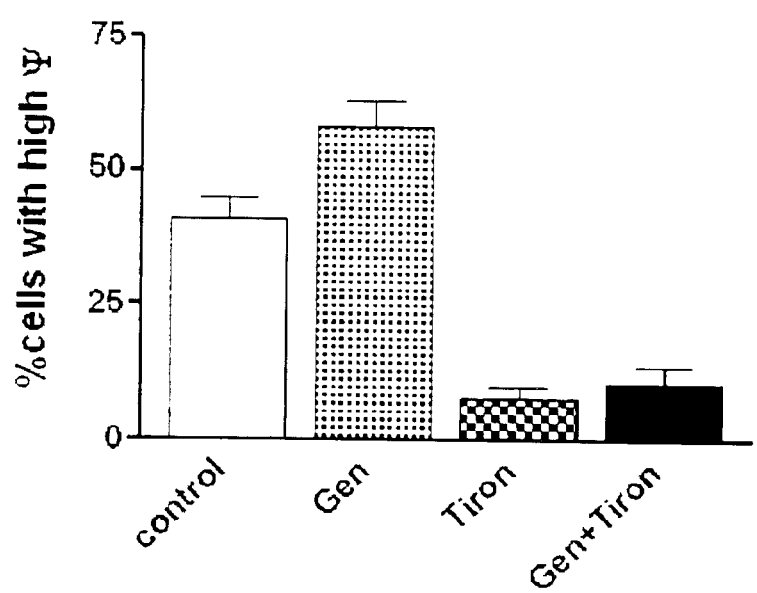

As shown in FIG. 11, trans-resveratrol alone and genistein alone have no effects on mitochondrial membrane potential. Additionally, DPI and Tiron markedly depolarized the mitochondrial membrane and the depolarization was not changed by the addition of trans-resveratrol or genistein. Thus, in the presence of serum, the production of ROS is essential for the maintenance of mitochondrial membrane polarity and the ability of polyphenolic compounds to potentiate the effects of ROS inhibitors on apoptosis is not due to changes in membrane polarity.

EXAMPLE 6

Effects of Inhibitors of PTP

A. POLYPHENOLIC COMPOUND ALONE

In order to determine the role of the cancer cell's PTP in the effects of the polyphenolic compounds on mitochondrial function, caspase-3 activation and apoptosis, we performed the following experiments. Mia PACA-2 cells were cultured in the absence of serum or growth factors for 24 hours in the presence or absence of quercetin (100 μM), trans-resveratrol (100 μM), Z-VAD FMK (50 μM), cyclosporin A (5 μM) and/or aristolochic acid (50 μM). Cells were collected, washed with ice-cold PBS and resuspended in lysis buffer comprising 0.5% Nonidet P-40 or manufactured by the name IGEPAL CA-630, 0.5 mM EDTA, 150 mM NaCl and 50 mM Tris at pH 7.5. Cell lysates were placed for 30 minutes on a rotator at 4° C. and then centrifuged for 15 minutes at 15,000 g. Cytosolic protein extracts (supernatants) were collected, protein concentrations were determined and the extracts were aliquoted and stored at −80° C. Cytosolic extracts were subjected to SDS-PAGE and Western blot was performed with an antibody against cytochrome c. Blots were then stripped and re-probed with an antibody against tubulin to confirm equal protein loading. The experiment was repeated twice with similar results.

Mia PACA-2 cells were cultured in the absence of serum or growth factors for 24 hours in the presence or absence of quercetin (100 μM), trans-resveratrol (100 μM), Z-VAD FMK (50 μM), cyclosporin A (5 μM) and/or aristolochic acid (50 μM). Enzyme assays were carried out at 37° C. in a buffer comprising 25 mM HEPES (pH 7.5), 10% sucrose, 0.1% CHAPS and 10 mM DTT with 800 g cytosolic protein and 20 μM of specific fluorogenic substrate. For caspase-3, the substrate was K-AspGluValAsp-AMC (z-DEVD). Cleavage of the caspase substrate releases AMC (7-amino-4-methylcoumarin), which emits a fluorescent signal with excitation at 380 nm and emission at 440 nm. The reaction was started by addition of caspase-3 substrate, the readings were taken at 0, 60, 90, and 120 minutes. Fluorescence was calibrated using a standard curve for AMC. The results were normalized to the DEVDase activity in cells not treated with polyphenolic compounds. The data were expressed as mol AMC/mg protein/min.

Mia PACA-2 cells were cultured in the absence of serum or growth factors for 24 hours in the presence or absence of quercetin (100 μM), trans-resveratrol (100 EM), Z-VAD FMK (50 μM), cyclosporin A (5 μM) and aristolochic acid (50 μM). The samples were analyzed by annexin staining as provided above.

Figure 12:
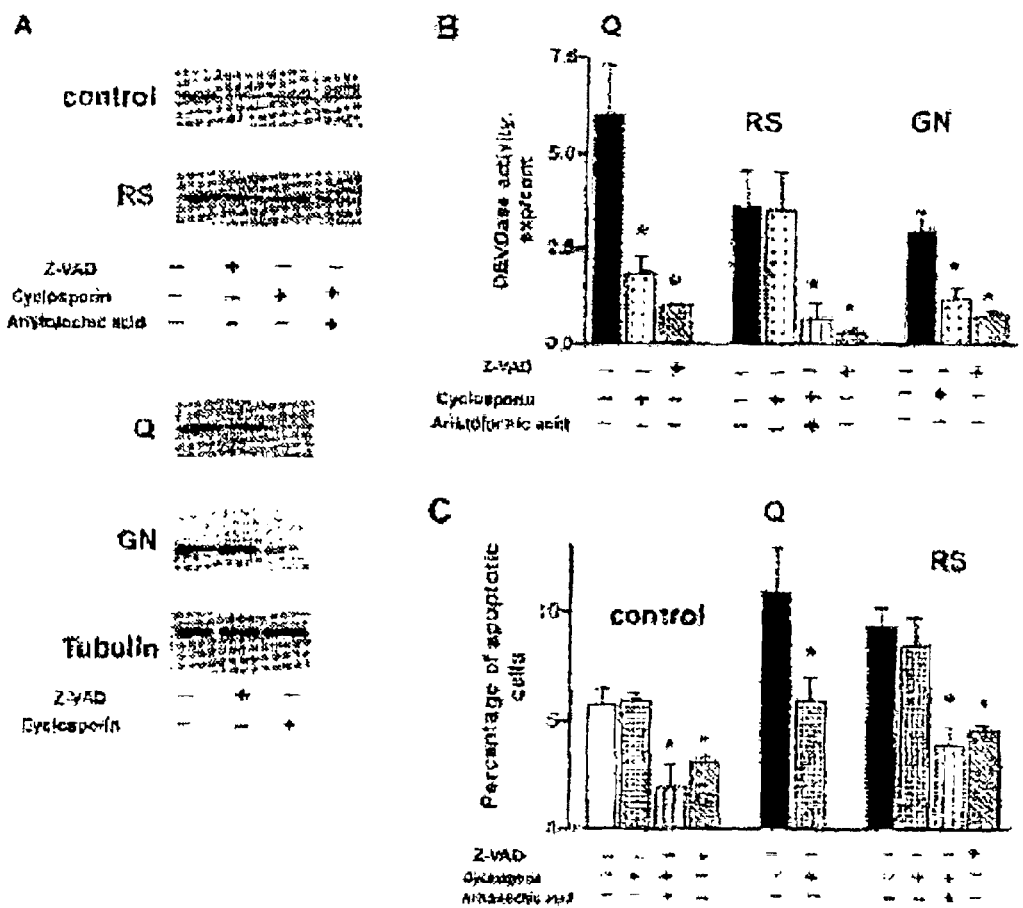
FIG. 12A shows that inhibition of PTP by cyclosporin A alone or in combination with aristolochic acid prevents release of mitochondrial cytochrome c release in MiaPACA-2 cancer cells treated with trans-resveratrol, quercetin and genistein. Z-VAD prevents mitochondrial cytochrome c release in untreated (control) cells. Q=quercetin, RS=trans-resveratrol, GN=genistein.
FIG. 12B shows that inhibition of PTP by cyclosporine A and aristolochic acid attenuates caspase-3 activity in Mia PACA-2 cells treated with polyphenolic compounds. The caspase inhibitor Z-VAD blocked caspase activity in the MiaPACA-2 cells. Q=quercetin, RS=trans-resveratrol, GN=genistein. The values represent means±SE (n=3). *p<0.05 compared to cells treated with the polyphenolic compound alone.
FIG. 12C shows that inhibition of PTP by cyclosporin A and aristolochic acid and inhibition of caspases by Z-VAD decreases apoptosis in MiaPACA-2 cells treated with polyphenolic compounds. Q=quercetin, RS=trans-resveratrol, GN=genistein. The values represent means±SE (n=3). *p<0.05 compared to untreated cells.

Cyclosporin A inhibits PTP channels by interacting with one of the key subunits of the PTP, cyclophilin, and cyclosporin A by itself or in combination with aristolochic acid blocks cytochrome c release on several cell types. As illustrated in FIG. 12A, Z-VAD inhibited the release of cytochrome c into the cytoplasm in control (untreated) cells. In contrast, Z-VAD had no effect on cytosolic cytochrome c release caused by quercetin or trans-resveratrol, thereby indicating that their action is directly on the mitochondria and not through the pathway involving caspase-8 and Bid. The cytochrome c release caused by quercetin and genistein were inhibited by cyclosporin A alone, whereas the cytochrome c release caused by trans-resveratrol required both cyclosporin A and aristolochic acid for inhibition.

As shown in FIG. 12B, cyclosporin A alone inhibited caspase-3 activity in quercetin and genistein treated cells, whereas both cyclosporin A and aristolochic acid were required to inhibit caspase-3 activity in trans-resveratrol-treated cells. As shown in FIG. 12C, cyclosporin A alone inhibited apoptosis in quercetin-treated cells, whereas both cyclosporin A and aristolochic acid were required to inhibit apoptosis caused by trans-resveratrol. These results indicate that polyphenolic compounds cause apoptosis from their direct effects on the cancer cell mitochondrial PTP to cause cytochrome c release which, in turn, activates caspase-3 leading to apoptosis.

B. COMBINATION

In order to determine the effect of a combination of trans-resveratrol and quercetin on cytochrome c release and caspase-3 activity, the following was conducted. Mia PACA-2 cells were cultured in the absence of serum or growth factors for 24 hours in the presence or absence of trans-resveratrol (25 μM), quercetin (25 μM), or the combination of trans-resveratrol (25 μM) and quercetin (25 μM). Cytosolic extracts were prepared and subject to SDS-PAGE followed by protein transfer. Immunoblot was performed with an antibody against tubulin to confirm equal protein loading.

Figure 13:
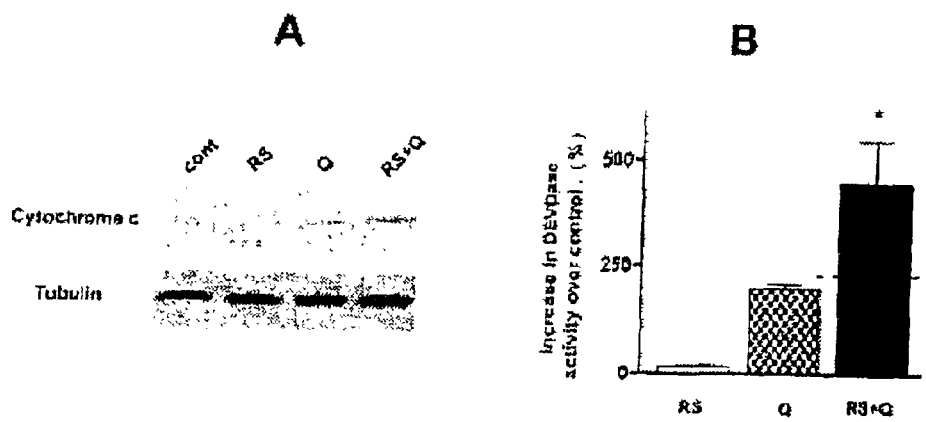
FIG. 13A is an immunoblot that shows the effect of polyphenolic compounds alone and in combination on cytochrome c release in Mia PACA-2 cells. Q=quercetin, RS=trans-resveratrol.
FIG. 13B shows the effect of polyphenolic compounds alone and in combination on caspase-3 activity in Mia PACA-2 cells. Q=quercetin, RS=trans-resveratrol. The values for trans-resveratrol, quercetin and the combination represent the means±SE (n=3) with the values for the controls subtracted. The dashed line over the bar for the values for trans-resveratrol plus quercetin represents the "predicted" additive values for the response to both agents. The recorded values were statistically significantly greater than the "predicted" additive values (p<0.05).

Mia PACA-2 cells were cultured in the absence of serum or growth factors for 24 hours in the presence or absence of trans-resveratrol (25 μM), quercetin (25 μM), or the combination of trans-resveratrol (25 μM) and quercetin (25 μM). Caspase-3 activity was measured in cell lysates with a fluorgenic assay using DEVD-AMC as a substrate. The results were normalized to the DEVDase activity in untreated cells. As illustrated in FIG. 13, the combinations resulted in responses of cytochrome c release and caspase-3 activity that were significantly greater than the additive responses.

EXAMPLE 7

NF-κB Assays

I. POLYPHENOLIC COMPOUND ALONE

In order to determine the role of activated NF-κB in the regulation of apoptosis caused by the polyphenolic compound, the following assay was conducted. BSp73AS cells were cultured for 6 hours and Mia PACA-2 cells were cultured in the absence of serum or growth factors for 24 hours in the absence (controls) or presence of rutin, quercetin, trans-resveratrol, or genistein, each at 100 μM and 20 μM proteosome inhibitor MG-132. Nuclear proteins were isolated and analyzed for NF-κB DNA binding activity with electrophoretic mobility shift assay (EMSA).

Specifically, aliquots of nuclear extracts with equal amount of protein, about 2 to about 10 μg, were mixed in 20 μl reactions with a buffer comprising 10 mM HEPES (pH 7.6), 50 mM KCl, 0.1 mM EDTA, 1 mM DTT, 10% (vol/vol) glycerol and 3 μg poly[d (I-C)]. After aliquots were equilibrated on ice for 5 minutes, binding reactions were stared by addition of 20–60,000 counts/min (20 fM) of $^{32}$P-labeled DNA probes and allowed to proceed for 25–30 minutes at room temperature or up to 1 hour on ice. The oligonucleotide probe 5'-GCAGA<u>GGGGACTTTCC</u>GAGA (SEQ ID NO: 1) containing the κB binding motif (underlined) was annealed to the complementary oligonucleotide with a 5'-G overhang and end-labeled using Klenow DNA polymerase I. The samples were electrophoresed at room temperature in 0.5× TBE buffer (1×TBE 89 mM Tris base, 89 mM boric acid and 2 mM EDTA) on nondenaturing 4.5% polyacrylamide gel at 200 V. Gels were dried and directly analyzed in the PhosphorImager (Molecular Dynamics, Sunnyvale, Calif.). The experiment was repeated twice.

Figure 14:
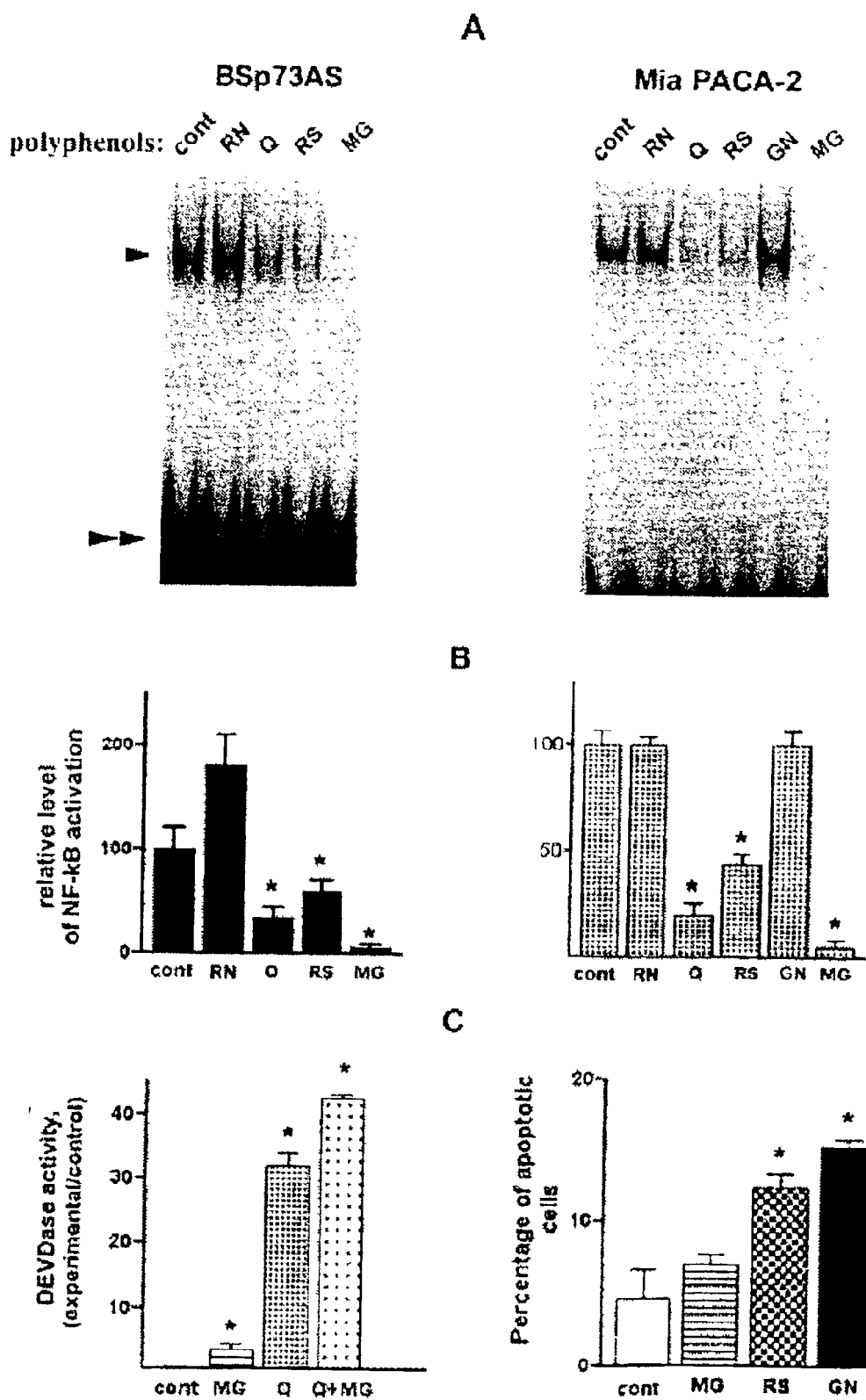
FIG. 14A shows that NF-κB is constitutively active in both BSp73As and Mia PACA-2 cells. Positions of specific NF-κB-DNA complexes and the free probe are indicated by single and double arrowheads, respectively. RN=rutin, Q=quercetin, RS=trans-resveratrol, GN=genistein, MG=MG-132.
FIG. 14B shows the relative NF-κB activities in cells treated with polyphenolic compounds or MG-132. The values represent densitometric intensities of NF-κB band quantified with PhosphorImager, relative to cells not treated with polyphenolic compounds or NF-κB inhibitors. Values represent means±SE (n=3). *p<0.05 as compared to control cells. RN=rutin, Q=quercetin, RS=trans-resveratrol, GN=genistein, MG=MG-132.
FIG. 14C shows caspase-3 activity and annexin staining in BSp73AS and Mia PACA-2 cells. The values represent means±SE (n=3). The results for caspase-3 were normalized to the DEVDase activity in untreated cells. *p<0.05 as compared to control cells. RN=rutin, Q=quercetin, RS=trans-resveratrol, GN=genistein, MG=MG-132.

As shown in FIG. 14A, NF-κB is constitutively active in both cancer cell lines. FIGS. 14A and 14B show that quercetin and trans-resveratrol inhibit NF-κB activation in both pancreatic cell lines, rutin activates NF-κB in BSp73AS cells but not Mia PACA-2 cells, and genistein has no effect on NF-κB in the Mia PACA-2 cells. The proteosome inhibitor, MG-132, blocks NF-κB activation in both cell lines. As shown in FIG. 14C, MG-132 causes a small increase in caspase-3 activity that adds to the caspase-3 activity caused by quercetin. Complete inhibition of NF-κB by MG-132 does not increase apoptosis rates to the same extent as trans-resveratrol which only partially inhibits NF-κB activation. Additionally, genistein causes significant apoptosis in the absence of an effect on NF-κB activation.

II. COMBINATIONS

To study the effects of combinations of DPI and polyphenolic compounds on serum-induced activation of NF-κB and protection from apoptosis, the following assay was conducted. Mia PACA-2 cells were cultured for 72 hours in the presence of serum with or without 100 μM trans-resveratrol, 15 μM DPI, a combination of trans-resveratrol, 100 μM genistein, or a combination of genistein and DPI. NF-κB binding activity was measured in nuclear extracts by gel shift assay as described above.

In order to demonstrate the cause and effect relationship between serum-induced activation of NF-κB and protection from apoptosis, NF-κB activation was inhibited and the effects on apoptosis in the presence and absence of polyphenolic compounds and ROS inhibitors were studied. In particular, Mia PACA-2 cells were cultured for 72 hours in the presence of serum with or without 50 μM trans-resveratrol (RS), 15 μM DPI, a combination of DPI and trans-resveratrol (RS+DPI), 10 μM MG-132 alone and in combination with RS, DPI, and RS+DPI. Internucleosomal DNA fragmentation was measured in cell lysates by cell death ELISA.

Figure 15:
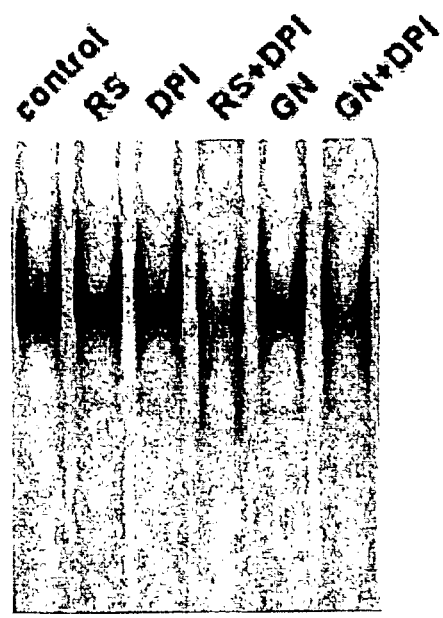
FIG. 15 shows the effects of combinations of DPI and polyphenolic compounds on NF-κB activation in the Mia PACA-2 pancreatic cancer cells. DPI=diphenylene iodonium; RS=trans-resveratrol; GN=genistein.
Figure 16:
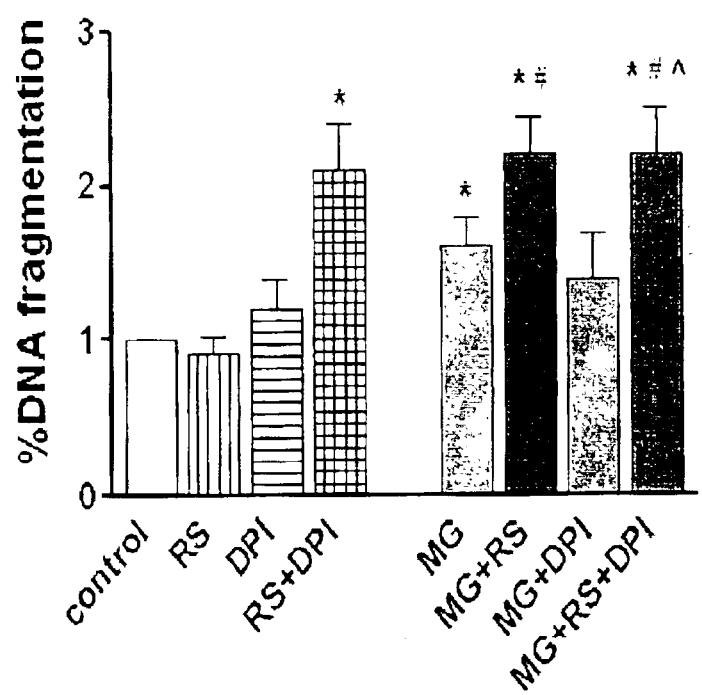
FIG. 16 shows the effects of MG-132, DPI and trans-resveratrol on oligonucleosomal DNA fragmentation in Mia PACA-2 pancreatic cancer cells. DPI=diphenylene iodonium; RS=trans-resveratrol; MG=MG-132. Values are means±SE (n=4). *p<0.05 compared to control cells. #p<0.05 compared to cells treated with MG-132 only. ^p<0.05 compared to cells treated with MG-132+DPI.

As shown in FIG. 15, the combination of a polyphenolic compound and a ROS inhibitor prevents NF-κB activation caused by serum. As shown in FIG. 16, trans-resveratrol in combination with MG-132 alone or MG-132 plus DPI increased apoptosis to a greater degree than that observed with MG-132 alone or MG-132 plus DPI, thereby indicating that inhibition of NF-κB sensitizes the cancer cells to apoptosis caused by trans-resveratrol.

EXAMPLE 8

PI 3-Kinase Inhibition Assays

To determine whether phosphatidylinositol 3-kinase (PI 3-kinase) and Akt/PKB mediate the effects of serum on NF-κB activation and that the effects of polyphenolic compounds on NF-κB activation are due to an ability to inhibit PI 3-kinase, the following assays were conducted. Specifically, to determine the effects of serum, LY294002, a PI 3-kinase inhibitor, and genistein on Akt/PKB phosphorylation, Mia PACA-2 cells were cultured for 72 hours in the absence or presence of serum with or without 100 μM genistein (GN) or 50 μM LY294002. Western blots were performed on whole cell lysates as described above except that specific antibodies against phosphorylated and total Akt/PKB were used (Akt/PKB is Anti-pS473 AktpAB from Promega, Madison Wis. and total Akt is Akt ½ from Santa Cruz, Santa Cruz, Calif.). The membranes were then stripped and re-probed with an antibody against total Akt.

To determine the effects of LY29400 and DPI on NF-κB activation, Mia PACA-2 cells were cultured for 72 hours in the presence of serum and 15 μM DPI with or without 50 μM LY294002. NF-κB DNA binding activity was measured in nuclear extracts by gel shift assay as described above.

Figure 17:
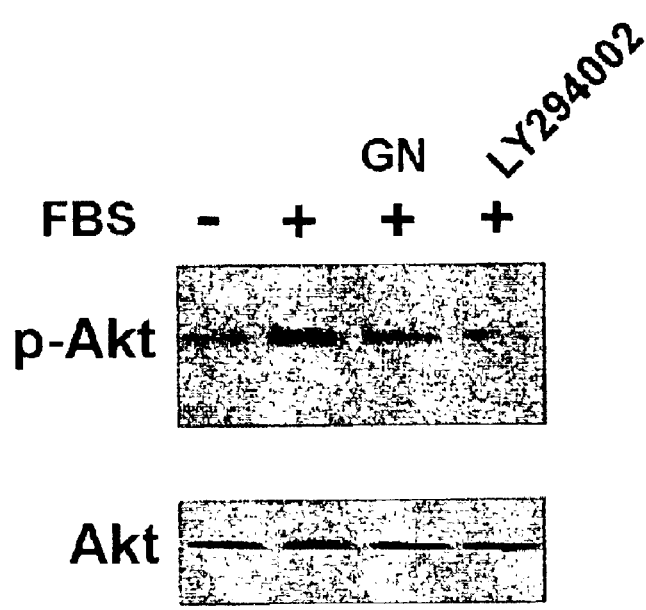
FIG. 17 shows the effects of serum, LY294002 and genistein on Akt/PKB phosphorylation in Mia PACA-2 pancreatic cancer cells. GN=genistein. The upper panels show representative Western blots performed on whole cell lysates using an antibody against phosphorylated Akt/PKB. The membranes were then stripped and re-probed with an antibody against total Akt (lower panel).
Figure 18:
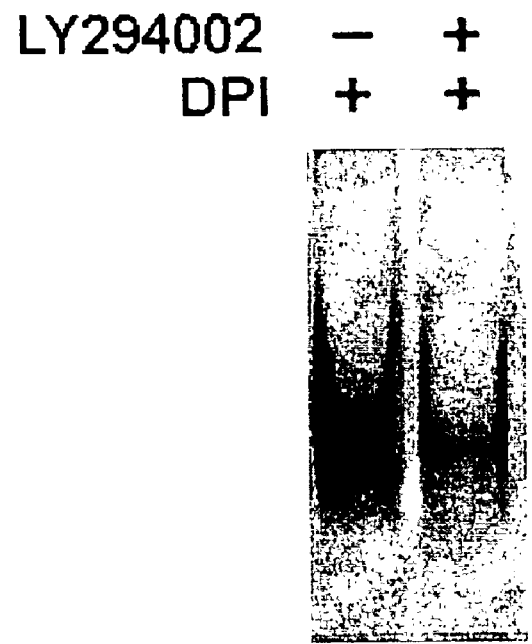
FIG. 18 shows the effects of LY294002 and DPI on NF-κB activation in Mia PACA-2 pancreatic cancer cells. DPI=diphenylene iodonium.

As shown in FIG. 17, serum increases the activated phosphorylated state of Akt/PKB, and LY294002 prevents the serum activation. Additionally, genistein attenuated serum-induced Akt phosphorylation/activation. As shown in FIG. 18, the combination of LY294002 and DPI inhibits NF-κB activation in a manner similar to the combination of a polyphenolic compound and DPI. These results indicate that polyphenolic compounds inhibit NF-κB activation through their effects on PI 3-kinase.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating or inhibiting pancreatic cancer in a subject comprising administering trans-resveratrol and diphenylene iodonium in a synergistically effective amount;

trans-resveratrol and Tiron in a synergistically effective amount;

genistein and diphenylene iodonium in a synergistically effective amount; or genistein and Tiron in a synergistically effective amount to the subject.

2. The method of claim 1, and further comprising administering at least one antioxidant to the subject.

3. The method of claim 1, wherein apoptosis is induced in the pancreatic cancer.

4. The method of claim 1, and further comprising administering MG-132, a proteasomal inhibitor, or both to the subject.

5. The method of claim 1, wherein the pancreatic cancer is a tumor.

6. The method of claim 5, wherein the tumor is a primary tumor.

7. The method of claim 4, wherein the tumor is metastatic.

8. The method of claim 1, wherein the pancreatic cancer is made susceptible to apoptosis by inhibiting or modulating NF-kB activity in the cancer.

9. The method of claim 1, wherein NF-kB activity is inhibited or modulated by administering to the subject an inhibitor of ROS production, NADPH oxidase, or both.

10. The method of claim 1, wherein NF-kB activity is inhibited or modulated by administering to the subject at least one antioxidant, at least one proteosomal inhibitor, or both.

11. The method of claim 1, wherein a composition comprising trans-resveratrol and diphenylene iodonium in a synergistically effective amount;

trans-resveratrol and Tiron in a synergistically effective amount;

genistein and diphenylene iodonium in a synergistically effective amount; or genistein and Tiron in a synergistically effective amount is administered to the subject.

12. The method of claim 11, wherein the composition further comprises at least one inhibitor of reactive oxygen species.

13. The method of claim 11, wherein the composition further comprises at least one antioxidant.

14. The method of claim 11, wherein the composition further comprises at least one antineoplastic agent.

15. The method of claim 11, wherein the composition is in the form of a pharmaceutical composition.

16. The method of claim 12, wherein the inhibitor of reactive oxygen species is an antioxidant.

* * * * *